US012678569B2

(12) United States Patent (10) Patent No.: US 12,678,569 B2

Mosebach et al. (45) Date of Patent: Jul. 14, 2026

(54) AUTOINJECTOR

(71) Applicant: Sanofi-Aventis Deutschland GMBH, Frankfurt am Main (DE)

(72) Inventors: Carsten Mosebach, Frankfurt am Main (DE); Thomas Kemp, Ashwell (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 18/082,253

(22) Filed: Dec. 15, 2022

(65) Prior Publication Data

US 2023/0126164 A1 Apr. 27, 2023

Related U.S. Application Data

(63) Continuation of application No. 16/521,266, filed on Jul. 24, 2019, now Pat. No. 11,541,188, which is a (Continued)

(30) Foreign Application Priority Data

Jul. 9, 2013 (EP) ..................................... 13175664

(51) Int. Cl.
| | | |
|---|---|---|
| *A61M 5/32* | (2006.01) | |
| *A61M 5/20* | (2006.01) | |
| *A61M 5/315* | (2006.01) | |

(52) U.S. Cl.
CPC ...... *A61M 5/31585* (2013.01); *A61M 5/2033* (2013.01); *A61M 5/3202* (2013.01); (Continued)

(58) Field of Classification Search
CPC .......... A61M 2205/273; A61M 5/3257; A61M 5/326; A61M 2005/3265; (Continued)

(56) References Cited

U.S. PATENT DOCUMENTS

| | | | |
|---|---|---|---|
| 5,137,516 A | 8/1992 | Rand et al. | |
| 5,295,965 A | 3/1994 | Wilmot | |
| | (Continued) | | |

FOREIGN PATENT DOCUMENTS

| | | |
|---|---|---|
| CH | 705345 | 2/2013 |
| CH | 705992 | 6/2013 |
| | (Continued) | |

OTHER PUBLICATIONS

EP Extended Search Report in European Application No. 13175664.5, dated Dec. 16, 2013, 6 pages.

(Continued)

*Primary Examiner* — Emily L Schmidt

(74) *Attorney, Agent, or Firm* — Fish & Richardson P.C.

(57) ABSTRACT

An autoinjector includes a case adapted to hold a medicament container having a needle, a needle shroud telescopically coupled to the case, and a plunger rotationally and slidably disposed in the case. The needle shroud is movable between a first extended position relative to the case in which the needle is covered and a retracted position relative to the case in which the needle is exposed. The plunger is rotatable relative to the case between a first rotational position in which the plunger is engaged to the case and a second rotational position in which the plunger disengages the case. The needle shroud is operably coupled to the plunger. When the needle shroud translates from the first extended position to the retracted position, the plunger rotates from the first rotational position to the second rotational position.

22 Claims, 23 Drawing Sheets

Related U.S. Application Data continuation of application No. 14/903,359, filed as application No. PCT/EP2014/064427 on Jul. 7, 2014, now Pat. No. 10,398,848.

(52) U.S. Cl.
CPC ................. *A61M 2005/206* (2013.01); *A61M 2005/3247* (2013.01); *A61M 2005/3267* (2013.01)

(58) Field of Classification Search
CPC .. A61M 2005/3267; A61M 2005/3263; A61M 2005/3268; A61M 2005/208
See application file for complete search history.

(56) References Cited

U.S. PATENT DOCUMENTS

| | | | |
|---|---|---|---|
| 5,658,259 A | 8/1997 | Pearson et al. | |
| 5,709,662 A | 1/1998 | Olive et al. | |
| 6,004,297 A | 12/1999 | Steenfeldt-Jensen et al. | |
| 6,277,099 B1 | 8/2001 | Strowe et al. | |
| 6,620,137 B2 | 9/2003 | Kirchhofer et al. | |
| 7,195,616 B2 | 3/2007 | Diller et al. | |
| 7,291,132 B2 | 11/2007 | DeRuntz et al. | |
| 7,297,135 B2 | 11/2007 | Jeffrey | |
| 7,341,575 B2 | 3/2008 | Rice et al. | |
| 7,500,963 B2 | 3/2009 | Westbye et al. | |
| 7,597,685 B2 | 10/2009 | Olson | |
| 7,635,348 B2 | 12/2009 | Raven et al. | |
| 7,645,265 B2 | 1/2010 | Stamp | |
| 7,678,085 B2 | 3/2010 | Graf | |
| 7,717,877 B2 | 5/2010 | Lavi et al. | |
| 7,771,397 B1 | 8/2010 | Olson | |
| 7,771,398 B2 | 8/2010 | Knight et al. | |
| 7,811,261 B2 | 10/2010 | Rubinstein et al. | |
| 7,976,494 B2 | 7/2011 | Kohlbrenner et al. | |
| 7,976,499 B2 | 7/2011 | Grunhut et al. | |
| 8,038,649 B2 | 10/2011 | Kronestedt | |
| 8,048,037 B2 | 11/2011 | Kohlbrenner et al. | |
| 8,062,255 B2 | 11/2011 | Brunnberg et al. | |
| 8,083,711 B2 | 12/2011 | Enggaard | |
| 8,157,768 B2 | 4/2012 | Haider et al. | |
| 8,323,238 B2 | 12/2012 | Croneberg et al. | |
| 8,357,125 B2 | 1/2013 | Grunhut et al. | |
| 8,361,025 B2 | 1/2013 | Lawlis et al. | |
| 8,366,668 B2 | 2/2013 | Maritan | |
| 8,366,680 B2 | 2/2013 | Raab | |
| 8,376,993 B2 | 2/2013 | Cox et al. | |
| 8,376,997 B2 | 2/2013 | Hogdahl et al. | |
| 8,403,883 B2 | 3/2013 | Fayyaz et al. | |
| 8,409,148 B2 | 4/2013 | Fiechter et al. | |
| 8,414,533 B2 | 4/2013 | Alexandersson | |
| 8,439,864 B2 | 5/2013 | Galbraith et al. | |
| 8,491,538 B2 | 7/2013 | Kohlbrenner et al. | |
| 8,568,359 B2 | 10/2013 | Carrel et al. | |
| 8,617,109 B2 | 12/2013 | Kronestedt et al. | |
| 8,617,124 B2 | 12/2013 | Wieselblad et al. | |
| 8,632,507 B2 | 1/2014 | Bartha | |
| 8,652,100 B1 | 2/2014 | Cowe | |
| 8,684,969 B2 | 4/2014 | Moller et al. | |
| 8,708,973 B2 | 4/2014 | Holmqvist | |
| 8,721,593 B2 | 5/2014 | Wozencroft | |
| 8,734,402 B2 | 5/2014 | Sharp et al. | |
| 8,758,292 B2 | 6/2014 | Tschirren et al. | |
| 8,771,237 B2 | 7/2014 | Markussen | |
| 8,808,250 B2 | 8/2014 | Ekman et al. | |
| 8,808,251 B2 | 8/2014 | Raab et al. | |
| 8,821,451 B2 | 9/2014 | Daniel | |
| 8,834,431 B2 | 9/2014 | Kohlbrenner et al. | |
| 8,840,591 B2 | 9/2014 | Raab et al. | |
| 8,882,723 B2 | 11/2014 | Smith et al. | |
| 8,911,411 B2 | 12/2014 | Nielsen | |
| 8,939,934 B2 | 1/2015 | Brereton et al. | |
| 8,945,063 B2 | 2/2015 | Wotton et al. | |
| 8,956,331 B2 | 2/2015 | Johansen et al. | |
| 8,961,463 B2 | 2/2015 | Edhouse et al. | |
| 8,961,473 B2 | 2/2015 | Heald | |
| 8,968,256 B2 | 3/2015 | Raab | |
| 8,968,258 B2 | 3/2015 | Nzike et al. | |
| 8,979,807 B2 | 3/2015 | Grunhut et al. | |
| 8,986,245 B2 | 3/2015 | Karlsson et al. | |
| 8,992,484 B2 | 3/2015 | Radmer et al. | |
| 8,992,487 B2 | 3/2015 | Eich et al. | |
| 9,005,160 B2 | 4/2015 | Karlsson et al. | |
| 9,011,386 B2 | 4/2015 | Kronestedt et al. | |
| 9,011,387 B2 | 4/2015 | Ekman et al. | |
| 9,022,982 B2 | 5/2015 | Karlsson et al. | |
| 9,022,991 B1 | 5/2015 | Moeller | |
| 9,022,993 B2 | 5/2015 | Dasbach et al. | |
| 9,022,994 B2 | 5/2015 | Moser et al. | |
| 9,044,548 B2 | 6/2015 | Miller et al. | |
| 9,044,553 B2 | 6/2015 | James et al. | |
| 9,057,369 B2 | 6/2015 | Kohlbrenner et al. | |
| 9,061,104 B2 | 6/2015 | Daniel | |
| 9,067,024 B2 | 6/2015 | Roberts et al. | |
| 9,072,837 B2 | 7/2015 | Maritan | |
| 9,072,838 B2 | 7/2015 | Hogdahl | |
| 9,089,652 B2 | 7/2015 | Nzike et al. | |
| 9,108,002 B2 | 8/2015 | Markussen | |
| 9,125,988 B2 | 9/2015 | Karlsson | |
| 9,132,235 B2 | 9/2015 | Holmqvist | |
| 9,132,236 B2 | 9/2015 | Karlsson et al. | |
| 9,199,038 B2 | 12/2015 | Daniel | |
| 9,205,199 B2 | 12/2015 | Kemp et al. | |
| 9,216,256 B2 | 12/2015 | Olson et al. | |
| 9,233,213 B2 | 1/2016 | Olson et al. | |
| 9,233,214 B2 | 1/2016 | Kemp et al. | |
| 9,233,215 B2 | 1/2016 | Hourmand et al. | |
| 9,242,044 B2 | 1/2016 | Markussen | |
| 9,248,245 B2 | 2/2016 | Ekman et al. | |
| 9,272,098 B2 | 3/2016 | Hourmand et al. | |
| 9,283,326 B2 | 3/2016 | Kemp et al. | |
| 9,283,327 B2 | 3/2016 | Hourmand et al. | |
| 9,283,328 B2 | 3/2016 | Dasbach | |
| 9,308,327 B2 | 4/2016 | Marshall et al. | |
| 9,327,083 B2 | 5/2016 | Giambattista et al. | |
| 9,333,304 B2 | 5/2016 | Brereton et al. | |
| 9,339,607 B2 | 5/2016 | Langley et al. | |
| 9,352,088 B2 | 5/2016 | Ekman et al. | |
| 9,358,345 B2 | 6/2016 | Brereton et al. | |
| 9,358,351 B2 | 6/2016 | Ekman et al. | |
| 9,393,368 B2 | 7/2016 | Nzike et al. | |
| 9,408,976 B2 | 8/2016 | Olson | |
| 9,408,977 B2 | 8/2016 | Butler et al. | |
| 9,408,979 B2 | 8/2016 | Veasey et al. | |
| 9,415,165 B2 | 8/2016 | Cowe | |
| 9,421,336 B2 | 8/2016 | Ekman et al. | |
| 9,427,525 B2 | 8/2016 | Barrow-Williams et al. | |
| 9,427,527 B2 | 8/2016 | Dasbach et al. | |
| 9,446,195 B2 | 9/2016 | Kramer et al. | |
| 9,446,196 B2 | 9/2016 | Hourmand et al. | |
| 9,446,201 B2 | 9/2016 | Holmqvist | |
| 9,457,149 B2 | 10/2016 | Kemp et al. | |
| 9,457,152 B2 | 10/2016 | Raab et al. | |
| 9,492,622 B2 | 11/2016 | Brereton et al. | |
| 9,662,452 B2 | 5/2017 | Daniel | |
| 9,867,940 B2 | 1/2018 | Holmqvist et al. | |
| 10,350,356 B2 | 7/2019 | Hirschel et al. | |
| 10,398,848 B2 | 9/2019 | Mosebach et al. | |
| 10,420,898 B2 | 9/2019 | Daniel | |
| 10,525,206 B2 | 1/2020 | Kemp | |
| 10,569,019 B2 | 2/2020 | Hirschel et al. | |
| 10,646,654 B2 | 5/2020 | Mosebach et al. | |
| 10,799,647 B2 | 10/2020 | Hostettler et al. | |
| 10,881,799 B2 | 1/2021 | Hirschel et al. | |
| 11,058,827 B2 | 7/2021 | Mosebach et al. | |
| 11,197,958 B2 | 12/2021 | Ekman et al. | |
| 11,383,044 B2 | 7/2022 | Tschirren et al. | |
| 11,541,188 B2 | 1/2023 | Mosebach et al. | |
| 11,660,396 B2 | 5/2023 | Mosebach et al. | |
| 11,850,401 B2 | 12/2023 | Swanson et al. | |
| 12,233,244 B2 | 2/2025 | Mosebach et al. | |
| 2002/0095120 A1 | 7/2002 | Larsen et al. | |

(56)  References Cited

U.S. PATENT DOCUMENTS

| | | |
|---|---|---|
| 2003/0105430 A1 | 6/2003 | Lavi et al. |
| 2004/0039336 A1 | 2/2004 | Amark et al. |
| 2005/0033230 A1* | 2/2005 | Alchas .............. A61M 5/326 |
| | | 604/117 |
| 2005/0101919 A1 | 5/2005 | Brunnberg et al. |
| 2005/0165360 A1 | 7/2005 | Stamp |
| 2007/0173770 A1 | 7/2007 | Stamp |
| 2008/0147006 A1 | 6/2008 | Brunnberg et al. |
| 2008/0228147 A1 | 9/2008 | David-Hegerich et al. |
| 2009/0005735 A1 | 1/2009 | Wikner et al. |
| 2009/0012471 A1 | 1/2009 | Harrison |
| 2009/0270804 A1* | 10/2009 | Mesa ..................... A61M 5/24 |
| | | 604/111 |
| 2010/0069846 A1 | 3/2010 | Stamp |
| 2010/0130930 A1 | 5/2010 | Stamp et al. |
| 2010/0137801 A1 | 6/2010 | Streit et al. |
| 2010/0152655 A1 | 6/2010 | Stamp |
| 2010/0152659 A1 | 6/2010 | Streit et al. |
| 2010/0185178 A1 | 7/2010 | Sharp et al. |
| 2010/0262083 A1 | 10/2010 | Grunhut et al. |
| 2010/0268169 A1 | 10/2010 | Llewellyn-Hyde et al. |
| 2011/0319864 A1 | 12/2011 | Beller et al. |
| 2012/0041387 A1 | 2/2012 | Bruggemann et al. |
| 2012/0053528 A1 | 3/2012 | Bollenbach et al. |
| 2012/0172817 A1 | 7/2012 | Bruggemann et al. |
| 2012/0203186 A1 | 8/2012 | Vogt et al. |
| 2012/0253289 A1 | 10/2012 | Cleathero |
| 2012/0316508 A1 | 12/2012 | Kirchhofer |
| 2013/0018313 A1 | 1/2013 | Kramer et al. |
| 2013/0035642 A1 | 2/2013 | Daniel |
| 2013/0035644 A1 | 2/2013 | Giambattista et al. |
| 2013/0041327 A1 | 2/2013 | Daniel |
| 2013/0041328 A1 | 2/2013 | Daniel |
| 2013/0041347 A1 | 2/2013 | Daniel |
| 2013/0123710 A1 | 5/2013 | Ekman et al. |
| 2013/0190721 A1 | 7/2013 | Kemp et al. |
| 2013/0211330 A1 | 8/2013 | Pedersen et al. |
| 2013/0237914 A1 | 9/2013 | Alexandersson |
| 2013/0261556 A1 | 10/2013 | Jones et al. |
| 2013/0267897 A1 | 10/2013 | Kemp et al. |
| 2013/0274662 A1 | 10/2013 | Hourmand et al. |
| 2013/0274677 A1 | 10/2013 | Ekman et al. |
| 2013/0281942 A1 | 10/2013 | Teucher et al. |
| 2013/0289525 A1 | 10/2013 | Kemp et al. |
| 2013/0296796 A1 | 11/2013 | Hourmand et al. |
| 2013/0310744 A1 | 11/2013 | Brereton et al. |
| 2013/0310745 A1 | 11/2013 | Latham et al. |
| 2013/0310757 A1 | 11/2013 | Brereton et al. |
| 2013/0310758 A1 | 11/2013 | Wozencroft |
| 2013/0317427 A1 | 11/2013 | Brereton et al. |
| 2013/0317428 A1 | 11/2013 | Brereton et al. |
| 2013/0317430 A1 | 11/2013 | Brereton et al. |
| 2013/0317431 A1 | 11/2013 | Kramer et al. |
| 2013/0317434 A1 | 11/2013 | Fabien et al. |
| 2013/0317448 A1 | 11/2013 | Hourmand et al. |
| 2013/0317479 A1 | 11/2013 | Brereton et al. |
| 2013/0324924 A1 | 12/2013 | Brereton et al. |
| 2013/0324925 A1 | 12/2013 | Brereton et al. |
| 2013/0324935 A1 | 12/2013 | Brereton et al. |
| 2013/0324938 A1 | 12/2013 | Brereton et al. |
| 2013/0324939 A1 | 12/2013 | Brereton et al. |
| 2013/0345643 A1 | 12/2013 | Hourmand et al. |
| 2014/0046259 A1 | 2/2014 | Reber et al. |
| 2014/0088505 A1 | 3/2014 | Fabien et al. |
| 2014/0207106 A1 | 7/2014 | Bechmann et al. |
| 2014/0221974 A1 | 8/2014 | Bechmann et al. |
| 2014/0228769 A1 | 8/2014 | Karlsson et al. |
| 2014/0243741 A1 | 8/2014 | Kaufmann et al. |
| 2014/0243757 A1 | 8/2014 | Dasbach et al. |
| 2014/0257194 A1* | 9/2014 | Edhouse .......... A61M 5/31553 |
| | | 604/198 |
| 2014/0330214 A1 | 11/2014 | Olson |
| 2014/0336578 A1 | 11/2014 | Brereton et al. |
| 2014/0336590 A1 | 11/2014 | Hourmand et al. |
| 2014/0343508 A1 | 11/2014 | Hourmand et al. |

| | | |
|---|---|---|
| 2015/0051580 A1 | 2/2015 | Shain et al. |
| 2015/0100029 A1 | 4/2015 | Cowe et al. |
| 2015/0133872 A1 | 5/2015 | Smith et al. |
| 2015/0174325 A1 | 6/2015 | Young et al. |
| 2015/0209517 A1 | 7/2015 | Brunnberg et al. |
| 2015/0265772 A1 | 9/2015 | Maritan |
| 2015/0273157 A1 | 10/2015 | Kohlbrenner et al. |
| 2015/0283323 A1 | 10/2015 | Young et al. |
| 2016/0008541 A1 | 1/2016 | Hirschel et al. |
| 2016/0051767 A1 | 2/2016 | Higgins et al. |
| 2016/0058950 A1 | 3/2016 | Marsh et al. |
| 2016/0067415 A1 | 3/2016 | Bayer et al. |
| 2016/0067418 A1 | 3/2016 | Morris et al. |
| 2016/0089498 A1 | 3/2016 | Daniel |
| 2016/0144129 A1 | 5/2016 | Mosebach et al. |
| 2016/0144133 A1 | 5/2016 | Kemp |
| 2016/0151585 A1 | 6/2016 | Kemp |
| 2016/0193412 A1 | 7/2016 | Cereda et al. |
| 2016/0243315 A1 | 8/2016 | Perche et al. |
| 2016/0354556 A1 | 12/2016 | Zucker et al. |
| 2016/0367763 A1 | 12/2016 | Tschirren et al. |
| 2017/0021103 A1 | 1/2017 | Mosebach et al. |
| 2018/0064875 A1 | 3/2018 | Holmqvist |
| 2019/0374717 A1 | 12/2019 | Swanson et al. |
| 2019/0381251 A1 | 12/2019 | Mosebach et al. |
| 2020/0139047 A1 | 5/2020 | Hirschel et al. |
| 2020/0254181 A1 | 8/2020 | Mosebach et al. |
| 2021/0154407 A1 | 5/2021 | Hirschel et al. |
| 2021/0322683 A1 | 10/2021 | Mosebach et al. |
| 2023/0022361 A1 | 1/2023 | Heiniger et al. |
| 2023/0218827 A1 | 7/2023 | Scheurer et al. |
| 2024/0075209 A1 | 3/2024 | Swanson et al. |
| 2024/0325643 A1 | 10/2024 | Mosebach et al. |
| 2025/0170333 A1 | 5/2025 | Mosebach et al. |

FOREIGN PATENT DOCUMENTS

| | | |
|---|---|---|
| CN | 1244811 | 2/2000 |
| CN | 101119761 | 2/2008 |
| CN | 101454032 | 6/2009 |
| CN | 101868270 | 10/2010 |
| CN | 102186521 | 9/2011 |
| CN | 102686255 | 9/2012 |
| CN | 102821801 | 12/2012 |
| CN | 103764205 | 4/2014 |
| EP | 0956873 | 11/1999 |
| EP | 0991441 | 12/2003 |
| EP | 2399634 | 12/2011 |
| EP | 2468334 | 6/2012 |
| EP | 2468335 | 6/2012 |
| EP | 2489384 | 8/2012 |
| EP | 2606924 | 6/2013 |
| EP | 2606925 | 6/2013 |
| EP | 2742962 | 6/2014 |
| EP | 3650064 | 5/2020 |
| EP | 3381490 | 9/2020 |
| FR | 2654938 | 5/1991 |
| GB | 2438592 | 12/2007 |
| JP | 2002-528182 | 9/2002 |
| JP | 2007-500530 | 1/2007 |
| JP | 2009-533124 | 9/2009 |
| JP | 2010-540055 | 12/2010 |
| JP | 2010-540058 | 12/2010 |
| JP | 2013-529527 | 7/2013 |
| JP | 2013-146600 | 8/2013 |
| JP | 2014-500089 | 1/2014 |
| RU | 2011148399 | 6/2013 |
| WO | WO 1994/011041 | 5/1994 |
| WO | WO 1998/020923 | 5/1998 |
| WO | WO 1999/022790 | 5/1999 |
| WO | WO 1999/037343 | 7/1999 |
| WO | WO 1999/053979 | 10/1999 |
| WO | WO 2000/024441 | 5/2000 |
| WO | WO 2002/047746 | 6/2002 |
| WO | WO 2005/009515 | 2/2005 |
| WO | WO 2005/070481 | 8/2005 |
| WO | WO 2005/097238 | 10/2005 |
| WO | WO 2005/115507 | 12/2005 |
| WO | WO 2006/057604 | 6/2006 |

(56) References Cited

FOREIGN PATENT DOCUMENTS

| WO | WO 2006/079064 | | 7/2006 | | |
|----|----|----|----|----|----|
| WO | WO 2007/083115 | | 7/2007 | | |
| WO | WO 2007/099044 | | 9/2007 | | |
| WO | WO 2007/129324 | | 11/2007 | | |
| WO | WO 2007/131013 | | 11/2007 | | |
| WO | WO 2007/131025 | | 11/2007 | | |
| WO | WO 2007/132353 | | 11/2007 | | |
| WO | WO 2008/059385 | | 5/2008 | | |
| WO | WO 2008/155377 | | 12/2008 | | |
| WO | WO 2009/019440 | | 2/2009 | | |
| WO | WO 2009/040603 | | 4/2009 | | |
| WO | WO 2009/040607 | | 4/2009 | | |
| WO | WO 2009/040672 | | 4/2009 | | |
| WO | WO 2009/101591 | | 8/2009 | | |
| WO | WO 2009/114542 | | 9/2009 | | |
| WO | WO 2010/017650 | | 2/2010 | | |
| WO | WO 2010/066590 | | 6/2010 | | |
| WO | WO 2010/108116 | | 9/2010 | | |
| WO | WO 2010/136077 | | 12/2010 | | |
| WO | WO 2010/136078 | | 12/2010 | | |
| WO | WO 2010/136078 | A1 | 12/2010 | | |
| WO | WO 2011/012903 | | 2/2011 | | |
| WO | WO 2011/043714 | | 4/2011 | | |
| WO | WO 2011/048223 | | 4/2011 | | |
| WO | WO 2011/111006 | | 9/2011 | | |
| WO | WO 2011/123024 | | 10/2011 | | |
| WO | WO 2011/126439 | | 10/2011 | | |
| WO | WO 2012/000940 | | 1/2012 | | |
| WO | WO-2012000940 | A2 * | 1/2012 | .......... | A61M 5/2033 |
| WO | WO 2012/022810 | | 2/2012 | | |
| WO | WO 2012/045350 | | 4/2012 | | |
| WO | WO 2012/073032 | | 6/2012 | | |
| WO | WO 2012/085025 | | 6/2012 | | |
| WO | WO 2012/122643 | | 9/2012 | | |
| WO | WO 2013/034647 | | 3/2013 | | |
| WO | WO 2013/034651 | | 3/2013 | | |
| WO | WO 2013/058697 | | 4/2013 | | |
| WO | WO 2013/063707 | | 5/2013 | | |
| WO | WO 2014/009705 | | 1/2014 | | |
| WO | WO 2021/008839 | | 1/2021 | | |
| WO | WO 2021/160540 | | 8/2021 | | |
| WO | WO 2021/197804 | | 10/2021 | | |
| WO | WO 2022/069617 | | 4/2022 | | |
| WO | WO 2022/184388 | | 9/2022 | | |

OTHER PUBLICATIONS

EP Search Report in European Application No. 14162454.4, dated Oct. 8, 2014.

EP Third Party Observations in European Application No. 17197256.5, dated Sep. 22, 2021, 7 pages.

International Preliminary Report on Patentability in International Appln. No. PCT/EP2014/064427, dated Jan. 12, 2016, 6 pages.

International Preliminary Report on Patentability in International Appln. No. PCT/EP2015/056686, dated Oct. 4, 2016, 8 pages.

International Search Report and Written Opinion in International Appln. No. PCT/EP2014/064427, dated Oct. 17, 2014, 9 pages.

International Search Report and Written Opinion in International Appln. No. PCT/EP2015/056686, dated Jun. 20, 2015.

U.S. Appl. No. 15/125,014, filed Sep. 9, 2016, Carsten Mosebach.

U.S. Appl. No. 16/859,143, filed Apr. 27, 2020, Carsten Mosebach.

* cited by examiner

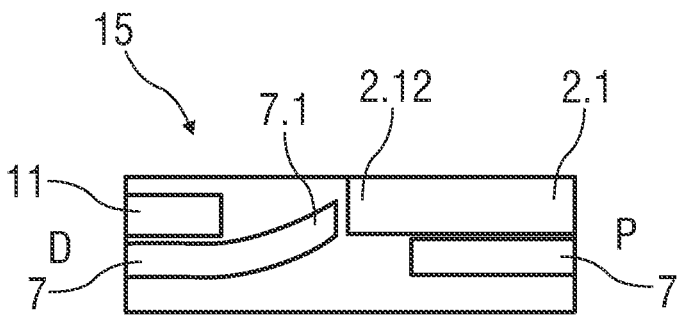
FIG 12
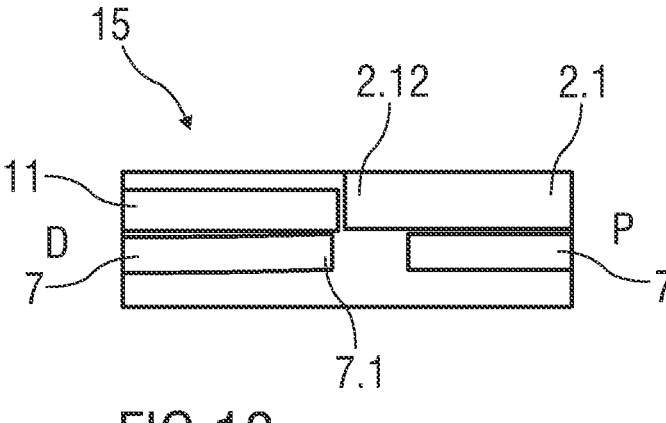
FIG 13
FIG 14

AUTOINJECTOR

CROSS-REFERENCE TO RELATED APPLICATIONS

This application is a continuation of U.S. patent application Ser. No. 16/521,266, filed Jul. 24, 2019, which is a continuation of U.S. patent application Ser. No. 14/903,359, filed Jan. 7, 2016, now U.S. Pat. No. 10,398,848, which is a U.S. national stage application under 35 USC § 371 of International Application No. PCT/EP2014/064427, filed on Jul. 7, 2014, which claims priority to European Patent Application No. 13175664.5, filed on Jul. 9, 2013, the entire contents of which are incorporated herein by reference.

TECHNICAL FIELD

The invention relates to an autoinjector.

BACKGROUND

Administering an injection is a process which presents a number of risks and challenges for users and healthcare professionals, both mental and physical. Injection devices typically fall into two categories—manual devices and auto-injectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Further, the force required to push the button/plunger may be too high (e.g., if the user is elderly or a child). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

There remains a need for an improved autoinjector.

SUMMARY

It is an object of the present invention to provide an improved autoinjector.

In an exemplary embodiment, an autoinjector according to the present invention comprises a case adapted to hold a medicament container having a needle, a needle shroud telescopically coupled to the case and movable between a first extended position relative to the case in which the needle is covered and a retracted position relative to the case in which the needle is exposed, and a plunger rotationally and slidably disposed in the case. The plunger is rotatable relative to the case between a first rotational position in which the plunger is engaged to the case and a second rotational position in which the plunger disengages the case. The needle shroud is operably coupled to the plunger. When the needle shroud translates from the first extended position to the retracted position, the plunger rotates from the first rotational position to the second rotational position.

In an exemplary embodiment, the needle shroud is movable from the retracted position to a second extended position relative to the case in which the needle is covered and the needle shroud cannot translate relative to the case.

In an exemplary embodiment, the autoinjector further comprises a cap removably coupled to the case. The cap may include an element adapted to engage a protective needle sheath removably disposed on the needle. The cap may include at least one compliant beam adapted to releasably engage at least one radial aperture in the needle shroud. When the cap is coupled to the case the at least one compliant beam engages the at least one radial aperture in the needle shroud and radially abuts the case. When the cap is removed from the case, the at least one compliant beam disengages the at least one radial aperture in the needle shroud and no longer radially abuts the case.

In an exemplary embodiment, the autoinjector further comprises a shroud spring biasing the needle shroud in a distal direction relative to the case.

In an exemplary embodiment, the autoinjector further comprises a drive spring biasing the plunger in a distal direction relative to the case. The plunger translates relative to the case under force of the drive spring when the plunger is in the second rotational position and the needle shroud is in the retracted position. The plunger may be at least partially hollow and the drive spring may be at least partially disposed within the plunger.

In an exemplary embodiment, the needle shroud includes at least one compliant shroud beam radially abutting the case when the needle shroud is in the first extended position and the retracted position, and the at least one compliant shroud beam deflects radially when the needle shroud is in the second extended position and axially abuts the case.

In an exemplary embodiment, the plunger includes a first plunger boss adapted to engage a shroud rib disposed on the needle shroud and a second plunger boss adapted to engage a case slot in the case. When the plunger is in the first rotational position and the needle shroud is in the first extended position, the first plunger boss engages the shroud rib and the second plunger boss engages the case slot. When the needle shroud translates from the first extended position to the retracted position, the plunger rotates from the first rotational position to the second rotational position and the second plunger boss disengages the case slot. The shroud rib maintains the plunger in the first rotational position when the needle shroud is in the first extended position. The needle shroud may include a receiving element adapted to receive the first plunger boss when the needle shroud is in the retracted position and the plunger is in the second rotational position.

In an exemplary embodiment, when the needle shroud translates from the first extended position to the retracted position, the shroud rib engages a plunger rib to rotate the plunger from the first rotational position to the second rotational position. The plunger rib may be disposed at an angle relative to a longitudinal axis of the case.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 12 is a schematic view of an exemplary embodiment of shroud lock mechanism of an exemplary embodiment of an autoinjector according to the present invention during assembly, FIG. 13 is a schematic view of an exemplary embodiment of shroud lock mechanism of an exemplary embodiment of an autoinjector according to the present invention during assembly, FIG. 14 is a schematic view of an exemplary embodiment of shroud lock mechanism of an exemplary embodiment of an autoinjector according to the present invention after assembly.

Corresponding parts are marked with the same reference symbols in all figures.

DETAILED DESCRIPTION

Figure 1A:
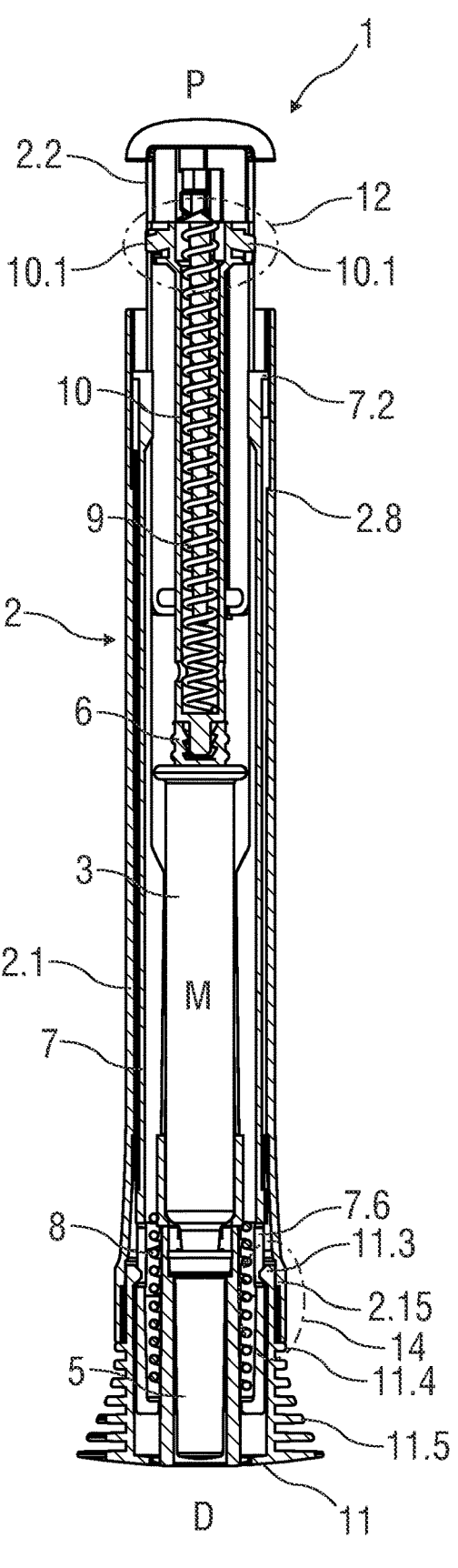
FIG. 1A is a longitudinal section of an exemplary embodiment of an autoinjector according to the present invention during assembly.

FIG. 1A is a longitudinal section of an exemplary embodiment of an autoinjector 1 according to the present invention during assembly. The autoinjector 1 comprises a case 2 comprising a front case 2.1 and a rear case 2.2. The case 2 is adapted to hold a medicament container, such as a syringe 3. The syringe 3 may be a pre-filled syringe and have a needle 4 arranged at a distal end. When the autoinjector 1 and/or the syringe 3 are assembled, a protective needle sheath 5 may be removably coupled to the needle 4. The protective needle sheath 5 may be a rubber needle sheath or a rigid needle sheath (which is composed of rubber and a full or partial plastic shell). A stopper 6 is arranged for sealing the syringe 3 proximally and for displacing a medicament M contained in the syringe 3 through the needle 4. In other exemplary embodiments, the medicament container may be a cartridge which includes the medicament M and engages a removable needle (e.g., by threads, snaps, friction, etc.).

In an exemplary embodiment, a cap 11 may be removably disposed at a distal end of the case 2. The cap 11 may include an element (e.g., a barb, a hook, a narrowed section, etc.) arranged to engage the protective needle sheath 5, the case 2 and/or a needle shroud 7 telescoped within the case 2. The cap 11 may comprise grip features 11.5 for facilitating removal of the cap 11 (e.g., by twisting and/or pulling the cap 11.5 relative to the case 2).

In an exemplary embodiment, a shroud spring 8 is arranged to bias the needle shroud 7 in a distal direction D against the case 2.

In an exemplary embodiment, a drive spring 9 is arranged within the case 2. A plunger 10 serves for forwarding a force of the drive spring 9 to the stopper 6. In an exemplary embodiment, the plunger 10 is hollow and the drive spring 9 is arranged within the plunger 10 biasing the plunger 10 in the distal direction D against the case 2. In another exemplary embodiment, the plunger 10 may be solid and the drive spring 9 may engage a proximal end of the plunger 10.

In an exemplary embodiment, a plunger release mechanism 12 is arranged for preventing release of the plunger 10 prior to retraction of the needle shroud 7 relative to the case 2 and for releasing the plunger 10 once the needle shroud 7 is sufficiently retracted.

In an exemplary embodiment, a first shroud lock mechanism 14 is arranged to prevent retraction of the needle shroud 7 relative to the case 2 when the cap 11 is in place, thereby avoiding unintentional activation of the autoinjector 1 (e.g., if dropped, during shipping or packaging, etc.). The first shroud lock mechanism 14 may comprise one or more compliant beams 11.3 on the cap 11 and a respective number of apertures 7.6 in the needle shroud 7 adapted to receive each of the compliant beams 11.3. When the cap 11 is attached to the autoinjector 1, the compliant beams 11.3 abut a radial stop 2.15 on the case 2 which prevents the compliant beams 11.3 from disengaging the apertures 7.6. When the cap 11 is attached to the autoinjector 1, axial movement of the cap 11 in the proximal direction P relative the case 2 is limited by a rib 11.4 on the cap 11 abutting the case 2. When the cap 11 is pulled in the distal direction D relative to the case 2, the compliant beams 11.3 may abut an edge of the aperture 7.6 and deflect to disengage the aperture 7.6, allowing for removal of the cap 11 and the protective needle sheath 5 attached thereto. In an exemplary embodiment, the compliant beams 11.3 and/or the apertures 7.6 may be ramped to reduce force necessary to disengage the compliant beams 11.3 from the apertures 7.6.

Figure 1B:
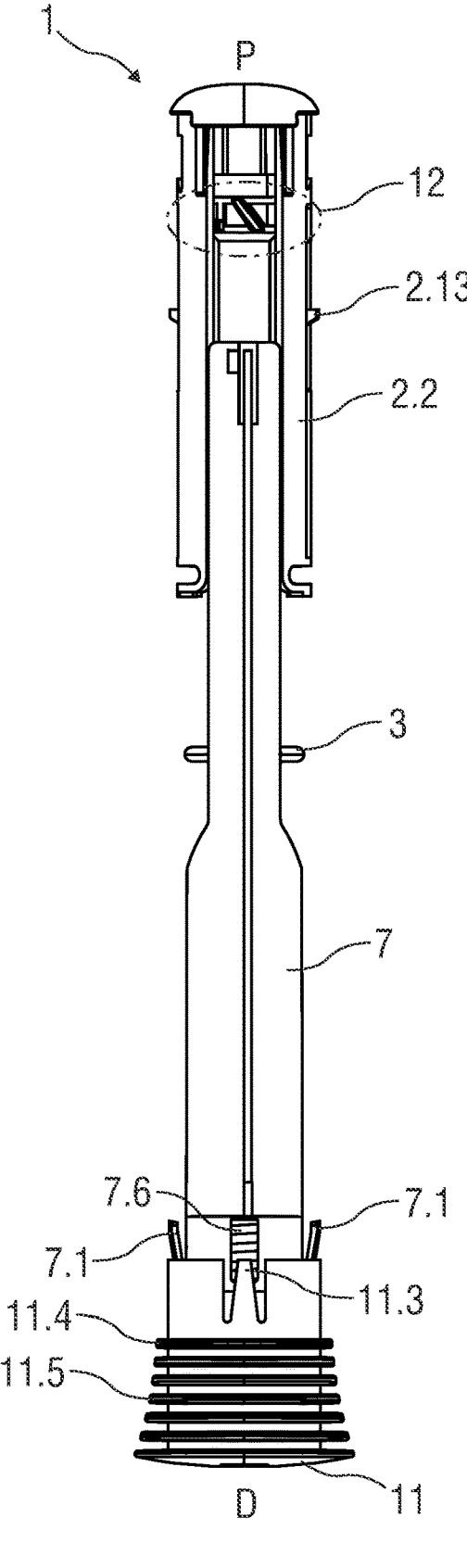
FIG. 1B is a schematic side view of an exemplary embodiment of an autoinjector according to the present invention during assembly.
Figure 2:
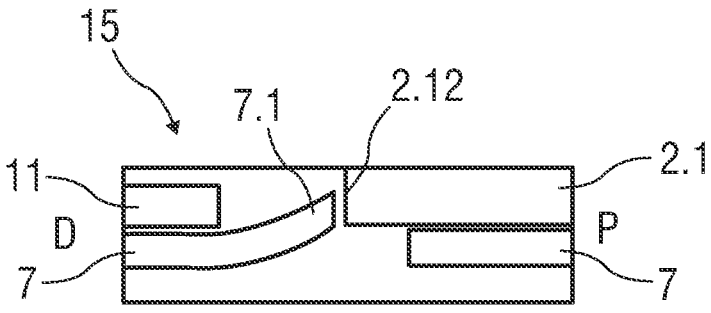
FIG. 2 is a schematic view of an exemplary embodiment of a shroud lock mechanism of an exemplary embodiment of an autoinjector according to the present invention.

FIG. 1B is a schematic side view of an exemplary embodiment of the autoinjector 1 according to the prevent invention during assembly. In the exemplary embodiment in FIG. 1B, the case 2 is removed for clarity. FIG. 1B and FIG. 2 show a second shroud lock mechanism 15 that is adapted to lock the needle shroud 7 in an axial position relative to the case 2 after the autoinjector 1 has been removed from the injection site. In an exemplary embodiment, the second shroud lock mechanism 15 comprises at least one compliant shroud beam 7.1 on the needle shroud 7 adapted to proximally abut a stop 2.12 on the case 2 after the autoinjector 1 has been removed from the injection site. The abutment of the shroud beam 7.1 on the stop 2.12 prevents translation of the needle shroud 7 in the proximal direction P relative to the case 2. Prior to use, when the cap 11 is attached to the autoinjector 1, the cap 11 is adapted to engage and deflect the compliant shroud beam 7.1 radially inward, allowing the shroud beam 7.1 to pass the stop 2.12 in the proximal direction P so that the needle shroud 7 can translate in the proximal direction P relative to the case 2.

In an exemplary embodiment, the autoinjector 1 may formed from at least two subassemblies, e.g., a control subassembly 1.1 and a drive subassembly 1.2, to allow for flexibility as to the time and location of manufacture of the subassemblies 1.1, 1.2 and final assembly with the syringe 3.

Figure 3:
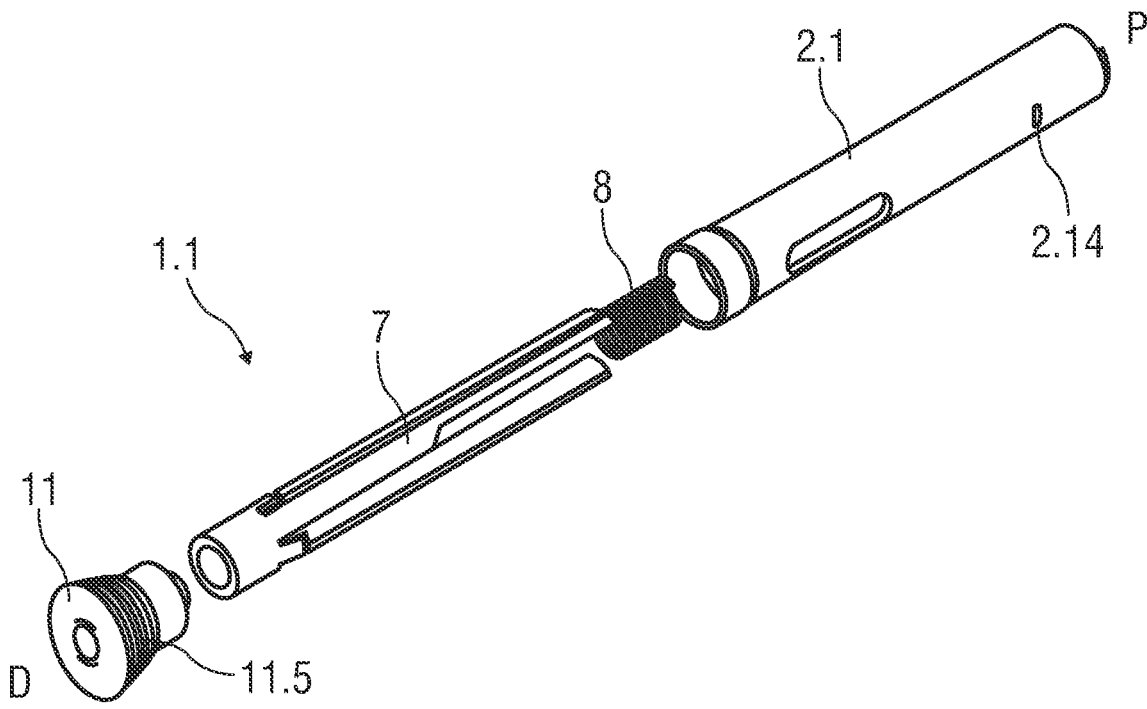
FIG. 3 is a perspective exploded view of an exemplary embodiment of a control subassembly of an exemplary embodiment of an autoinjector according to the present invention.

FIG. 3 is a perspective exploded view of an exemplary embodiment of a control subassembly 1.1 of an autoinjector 1 according to the present invention. In an exemplary embodiment, the control subassembly 1.1 comprises the cap 11, the needle shroud 7, the shroud spring 8 and the front case 2.1. To assemble the control subassembly 1.1, the shroud spring 8 is inserted into the needle shroud 7, and the needle shroud 7 with the shroud spring 8 is inserted into the front case 2.1. The cap 11 is arranged over the distal end of the needle shroud 7.

Figure 4:
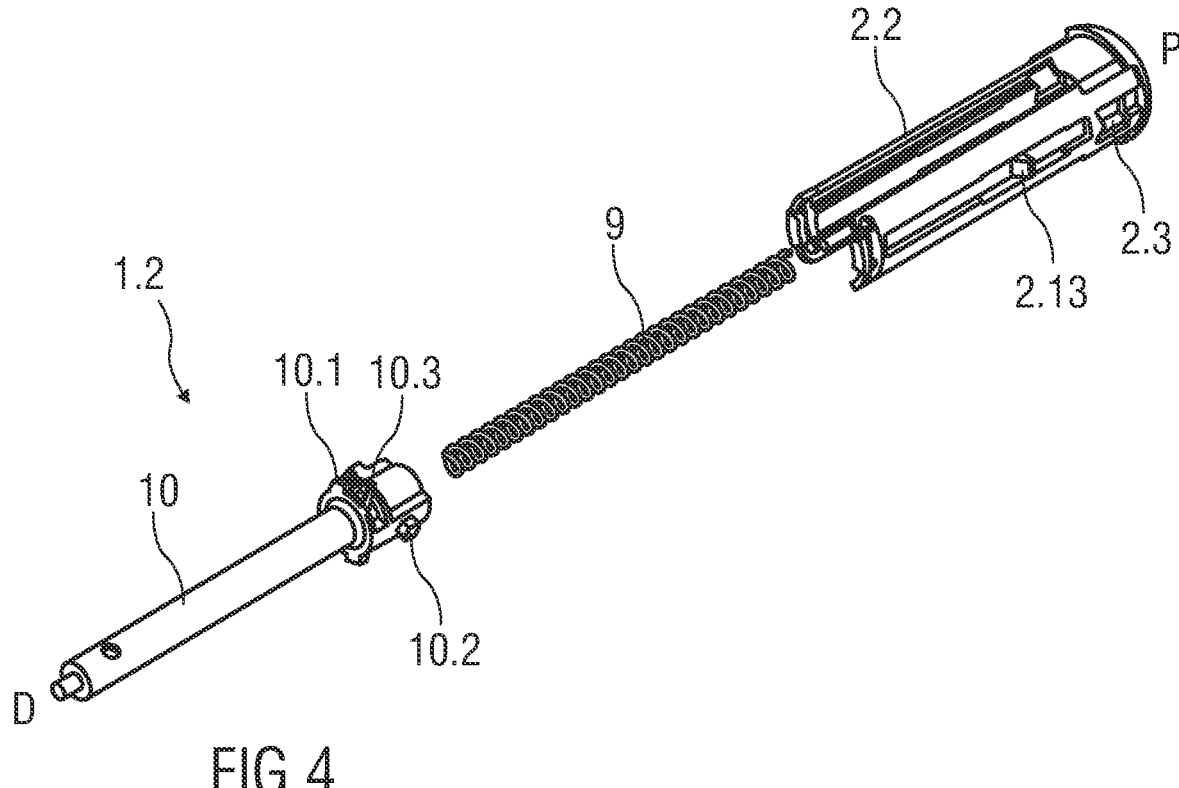
FIG. 4 is a perspective exploded view of an exemplary embodiment of a drive subassembly of an exemplary embodiment of an autoinjector according to the present invention.

FIG. 4 is a perspective exploded view of an exemplary embodiment of a drive subassembly 1.2 of an autoinjector 1 according to the present invention. In an exemplary embodiment, the drive subassembly 1.2 the plunger 10, the drive spring 9 and the rear case 2.2. Those of skill in the art will understand that if the viscosity or volume, for example, of the medicament M in the syringe 3 is changed, only parts of the drive subassembly 1.2 may need to be changed. To assemble the drive subassembly 1.2, the drive spring 9 is inserted into the plunger 10 and the plunger 10 is inserted in the rear case 2.2 in the proximal direction P thereby compressing the drive spring 9. Once the plunger 10 and the drive spring 9 reach a compressed position it is rotated by an angle, e.g. approximately 30° relative to the rear case 2.2, to engage the plunger 10 to the rear case 2.2. In an exemplary embodiment, the rear case 2.2 may have a cam surface to engage the plunger 10 to induce this rotation prior to the plunger 10 and the drive spring 9 reaching the compressed position.

Figure 5:
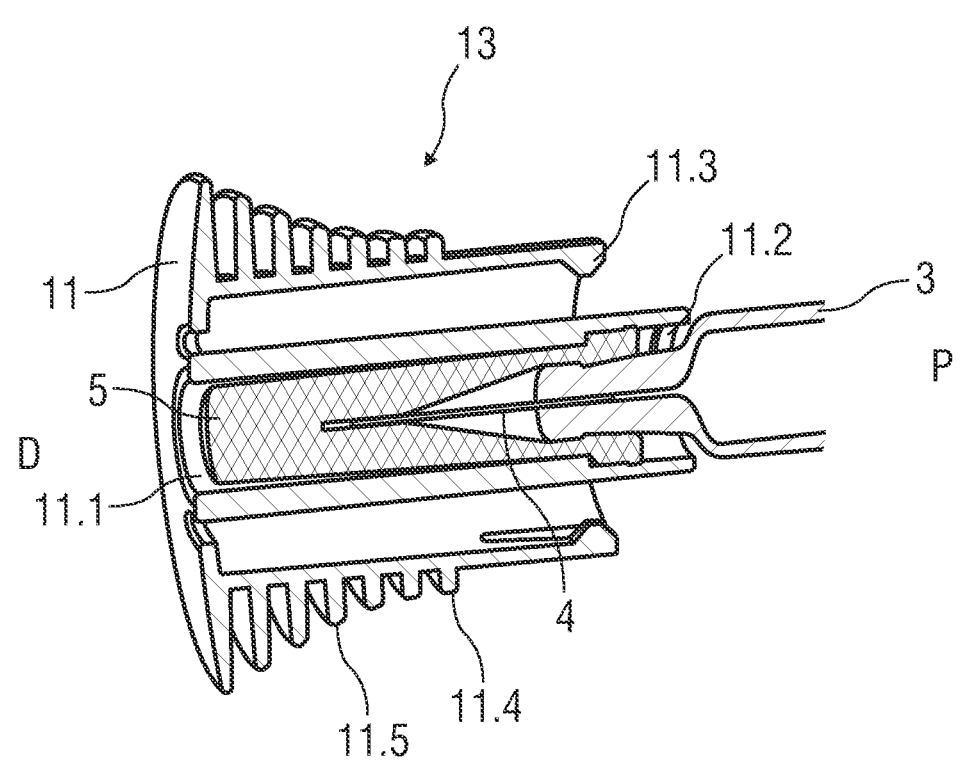
FIG. 5 is a perspective view of an exemplary embodiment of a needle sheath removal mechanism of an exemplary embodiment of an autoinjector according to the present invention.

FIG. 5 is a perspective view of an exemplary embodiment of a needle sheath removal mechanism 13 of an autoinjector 1 according to the present invention. The needle sheath removal mechanism 13 comprises an opening 11.1 axially arranged in the cap 11. The opening 11.1 is approximately sized and shaped to receive the protective needle sheath 5. One or more bosses 11.2 may be disposed on a proximal end of the cap 11 and adapted to abut the protective needle sheath 5. For example, when the protective needle sheath 5 is inserted into the opening 11.1, the protective needle sheath 5 may deform around the bosses 11.2. The bosses 11.2 may be ramped to reduce force necessary to insert the protective needle sheath 5 into the opening 11.1. Once the protective needle sheath 5 has passed the bosses 11.2 in the distal direction D, the bosses 11.2 may abut a proximal end of the protective needle sheath 5 to prevent translation of the protective needle sheath 5 in the proximal direction P relative to the cap 11. For example, during removal of the cap 11 from the autoinjector 1, the bosses 11.2 on the cap 11 may abut the proximal end of the protective needle sheath 5 and push the protective needle sheath 5 in the distal direction D off of the needle 4. with their non-ramped distal face. Those of skill in the art will understand that a number of parameters can be varied, e.g. a radial height of the boss 11.2, an axial length of the boss 11.2, an angle of the ramp of the boss 11.2, a durometer of the protective needle sheath 5, a surface finish of the boss 11.2, etc., which could increase or decrease assembly forces, cap removal forces, etc.

Figure 6:
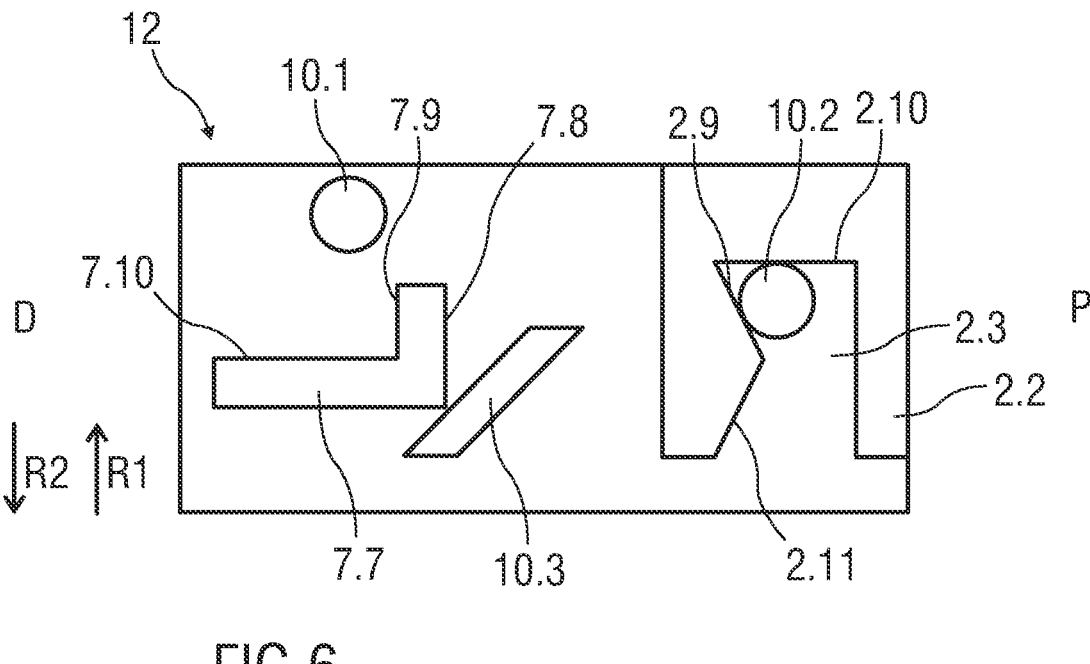
FIG. 6 is a schematic view of an exemplary embodiment of a plunger release mechanism of an exemplary embodiment of an autoinjector according to the present invention.

FIG. 6 is a schematic view of an exemplary embodiment of a plunger release mechanism 12 of the autoinjector 1 according to the present invention during assembly. The plunger release mechanism 12 is arranged for preventing release of the plunger 10 prior to retraction of the needle shroud 7 relative to the case 2 and for releasing the plunger 10 once the needle shroud 7 is sufficiently retracted. In an exemplary embodiment, the plunger release mechanism 12 comprises the plunger 10, the rear case 2.2, and the needle shroud 7 interacting with each other. In an exemplary embodiment, the needle shroud 7 is limited to axial movement relative to the case 2, and the plunger 10 can translate axially and rotate relative to the case 2.

In an exemplary embodiment, the plunger 10 comprises a first plunger boss 10.1 (e.g., a plunger protrusion or a shroud interaction portion) adapted to engage a shroud rib 7.7 (e.g., a shroud protrusion or a plunger interaction portion) on the needle shroud 7, a second plunger boss 10.2 adapted to engage a case slot 2.3 in the case 2, and a plunger rib 10.3 adapted to engage the shroud rib 7.7 on the needle shroud 7. In an exemplary embodiment, the shroud rib 7.7 is located on a needle shroud leg of the needle shroud. In an exemplary embodiment, the shroud rib 7.7 comprises a proximal face 7.8 adapted to engage the plunger rib 10.3, and a distal face 7.9 and a longitudinal face 7.10 adapted to engage the first plunger boss 10.1. A receiving element (e.g., a recess, a hole, etc.) may be formed on the needle shroud 7 distal of the longitudinal face 7.10 of the shroud rib 7.7. In an exemplary embodiment, the case slot 2.3 comprises a first angled surface 2.9 adapted to apply a rotational force in a first rotational direction R1 to the second plunger boss 10.2, a wall 2.10 adapted to abut the second plunger boss 10.2 to limit rotation of the plunger 10 relative to the case 2 in the first rotational direction R1, and a second angled surface 2.11 adapted to apply a rotational force in a second rotational direction R2, opposite the first rotational direction R1, to the second plunger boss 10.2.

In an exemplary embodiment of an assembly process of the drive subassembly 1.2, the plunger 10 with the drive spring 9 is inserted into the rear case 2.2. When the second plunger boss 10.2 is axially aligned with the case slot 2.3, the plunger 10 is rotated in the first rotational direction R1 until the second plunger boss 10.2 is moved into the case slot 2.3 until it abuts the wall 2.10. In this position, the first angled surface 2.9 prevents the second plunger boss 10.2 from moving in the second rotational direction R2, and thus prevents the plunger 10 from rotating relative to the case 2.

Figure 7:
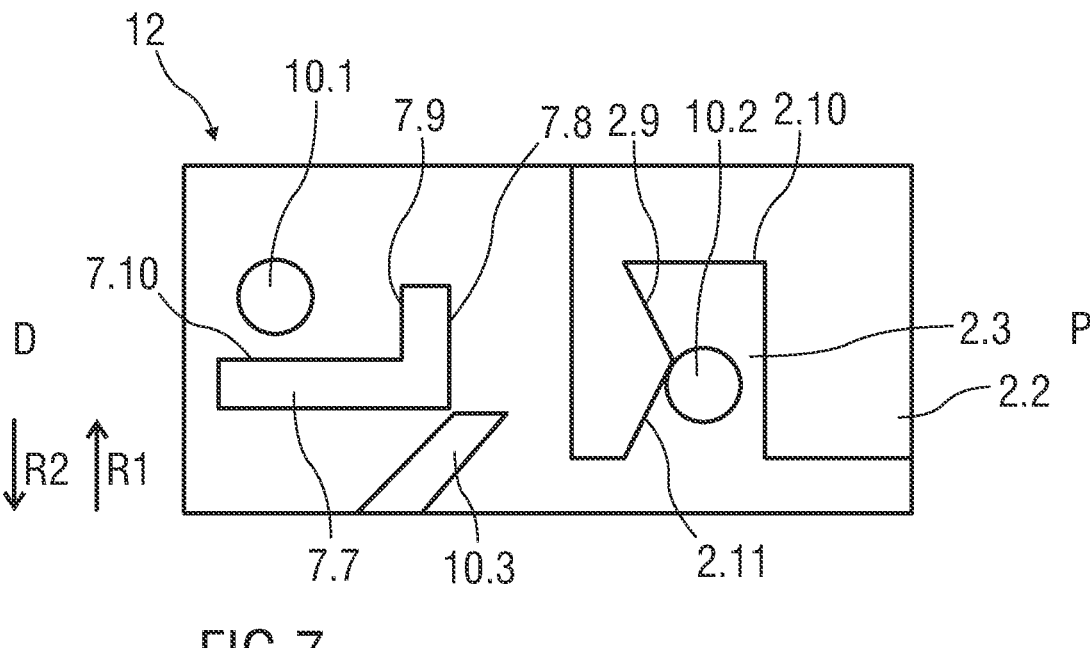
FIG. 7 is a schematic view of an exemplary embodiment of a plunger release mechanism of an exemplary embodiment of an autoinjector according to the present invention during assembly.

After a syringe 3 (with the protective needle sheath 5 disposed on the needle 4) is inserted into the control assembly 1.1, the drive subassembly 1.2 is coupled to the control subassembly 1.1. In an exemplary embodiment, a pair of resilient beams 2.13 (shown in FIG. 1B) on the rear case 2.2 is adapted to snap into recesses 2.14 (shown in FIG. 3) in the front case 2.1 to lock the drive subassembly 1.2 to the control subassembly 1.1. As the drive assembly 1.2 is coupled to the control subassembly 1.1, the needle shroud 7 translates proximally (e.g., by use of an assembly jig) causing the shroud rib 7.7 to abut the plunger rib 10.3. As shown in FIG. 7, as the shroud rib 7.7 pushes plunger rib 10.3, the angle of the plunger rib 10.3 causes the plunger 10 to rotate relative to the case 2 in the second rotational direction R2, and the second plunger boss 10.2 rides along the first angled surface 2.9 onto the second angled surface 2.11. When the second plunger boss 10.2 is disposed on the second angled surface 2.11, the force of the drive spring 9 imparts a rotational force on the plunger 10 in the second rotational direction R2 due to the angle of the second angled surface 2.11.

Figure 8:
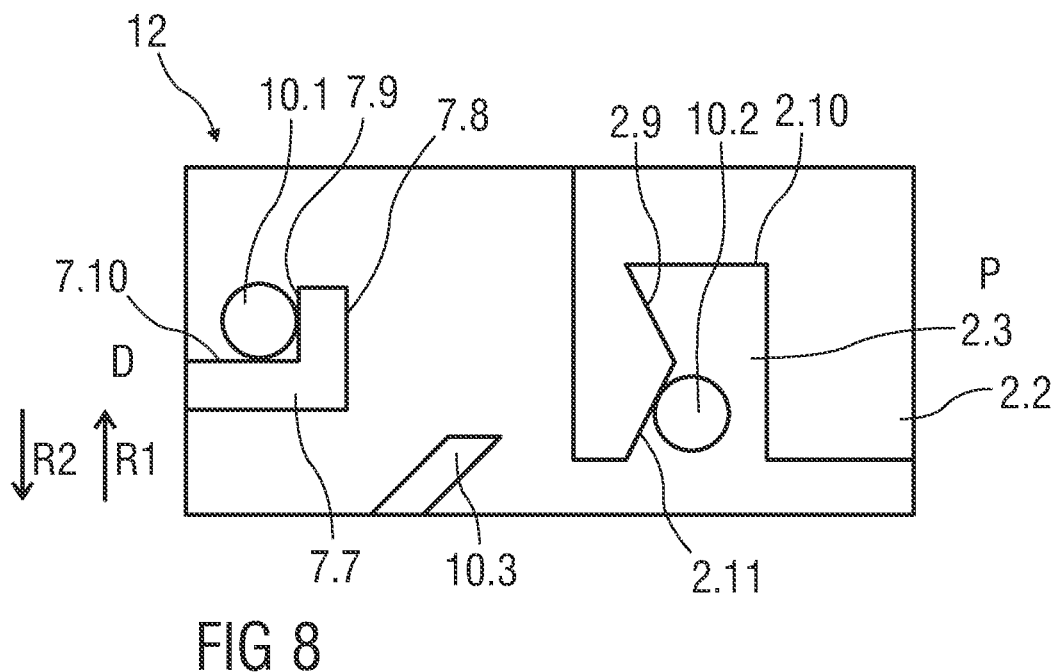
FIG. 8 is a schematic view of an exemplary embodiment of a plunger release mechanism of an exemplary embodiment of an autoinjector according to the present invention after assembly.

As shown in FIG. 8, when the needle shroud 7 is released (e.g., by removing the assembly jig), the needle shroud 7 translates in the distal direction D relative to the case 2 under the force the shroud spring 8 until the shroud rib 7.7 abuts the first plunger boss 10.1. For example, the distal face 7.9 of the shroud rib 7.7 may abut the first plunger boss 10.1 and maintain the needle shroud 7 in an axial position relative to the case 2. The second plunger boss 10.2 is prevented from disengaging the case slot 2.3, because the shroud rib 7.7 prevents the plunger 10 from rotating in the second rotational direction R2 relative to the case 2. For example, the longitudinal face 7.10 of the shroud rib 7.7 abuts the first plunger boss 10.1 to prevent rotation of the plunger 10.

Figure 9:
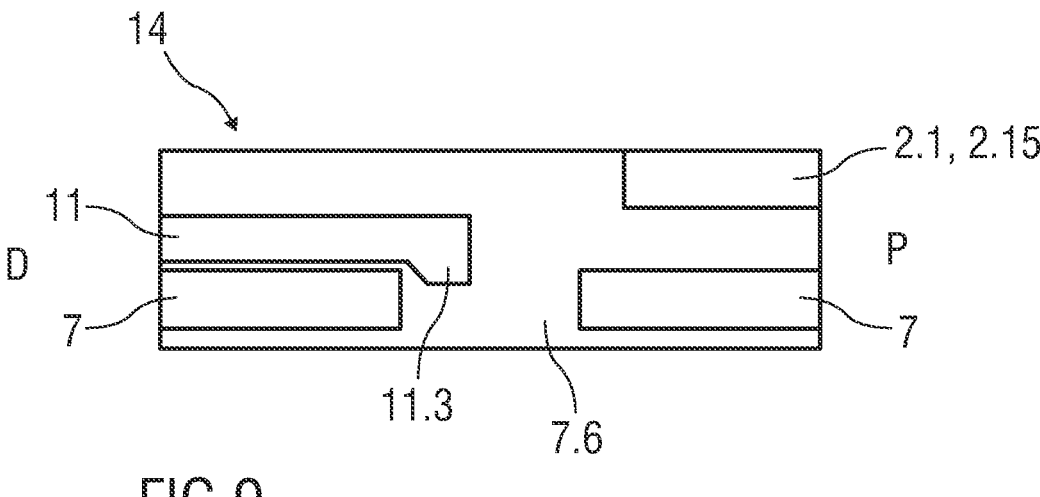
FIG. 9 is a schematic view of an exemplary embodiment of a shroud lock mechanism of an exemplary embodiment of an autoinjector according to the present invention after assembly.

FIG. 9 shows an exemplary embodiment of the first shroud lock mechanism 14 for an autoinjector 1 according to the present invention after assembly of the control subassembly 1.1. The compliant beam 11.3 on the cap is engaged in the aperture 7.6 within the needle shroud 7. The radial stop 2.15 is axially spaced from the compliant beam 11.3.

Figure 10:
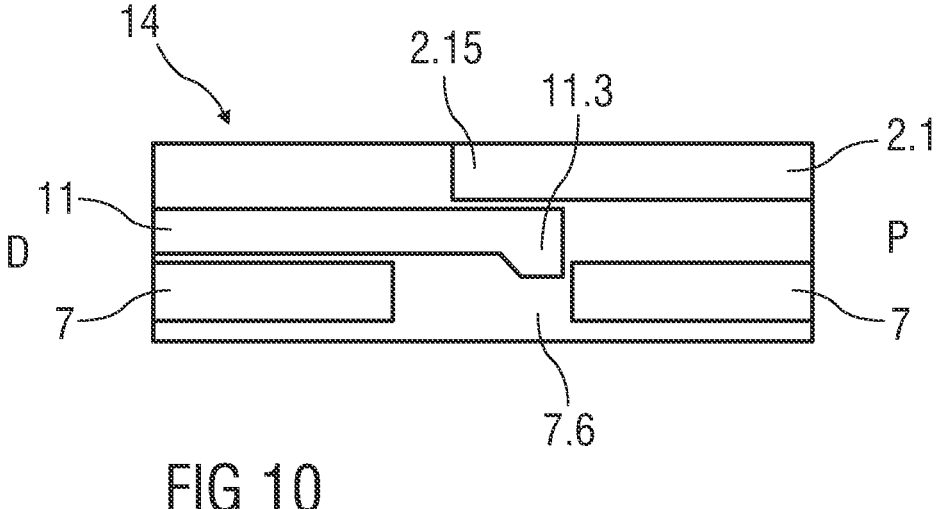
FIG. 10 is a schematic view of an exemplary embodiment of shroud lock mechanism of an exemplary embodiment of an autoinjector according to the present invention during assembly.

FIG. 10 shows an exemplary embodiment of the first shroud lock mechanism 14 for an autoinjector 1 according to the present invention during insertion of the syringe 3 into the control subassembly 1.1 for engaging the protective needle sheath 5 to the cap 11. The aperture 7.6 provides some clearance allowing a movement of the needle shroud 7 relative to the cap 11 in the distal direction D. The front case 2.1 is also moved in the distal direction D relative to the cap 11 axially aligning the radial stop 2.15 with the compliant beam 11.3 preventing the cap 11 from disengaging the needle shroud 7.

Figure 11:
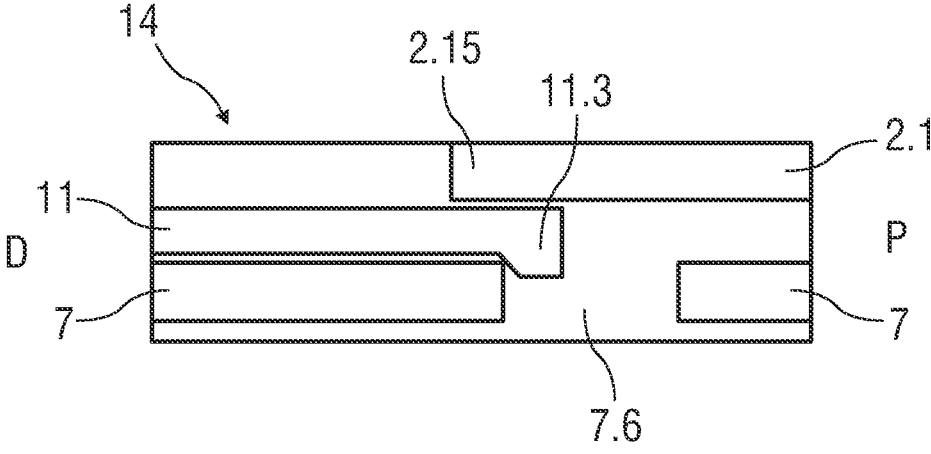
FIG. 11 is a schematic view of an exemplary embodiment of shroud lock mechanism of an exemplary embodiment of an autoinjector according to the present invention during assembly.

FIG. 11 shows an exemplary embodiment of the first shroud lock mechanism 14 for an autoinjector 1 according to the present invention, wherein after insertion of the syringe 3, the needle shroud 7 is moved further in the proximal direction P relative to the front case 2.1 by an assembly jig (not illustrated). In this state, the drive subassembly 1.2 may be assembled to the control subassembly 1.1. The compliant beam 11.3 remains engaged in the aperture 7.6 and the radial stop 2.15 prevents them from disengaging.

After assembly of the drive subassembly 1.2 to the control subassembly 1.1, the assembly jig is removed allowing the needle shroud 7 to move back in the distal direction D relative to the front case 2.1 under the force of the shroud spring 8 arriving again in the state illustrated in FIG. 10. In this configuration, the needle shroud 7 is prevented from moving in the proximal direction P relative to the case 2, because the radial stop 2.15 prevents the compliant beam 11.3 from disengaging the aperture 7.6 and the rib 11.4 on the cap 11 proximally abuts the front case 2.1.

FIG. 12 shows an exemplary embodiment of the second shroud lock mechanism 15 for an autoinjector 1 according to the present invention after assembly of the control subassembly 1.1. The needle shroud 7 is partially inserted into the cap 11. The shroud beam 7.1 is in a non-deflected position proximally abutting the stop 2.12 in the front case 2.1. This prevents the needle shroud 7 from moving further in the proximal direction P relative to the front case 2.1 and keeps the control subassembly 1.1 locked together.

FIG. 13 shows an exemplary embodiment of the second shroud lock mechanism 15 for an autoinjector 1 according to the present invention during insertion of the syringe 3 into the control subassembly 1.1, wherein the needle shroud 7 is moved further in the distal direction D into the cap 11 such that the cap 11 radially inwardly deflects the shroud beam 7.1 out of its abutment with the stop 2.12. The needle shroud 7 is thus free to move in the proximal direction P relative to the front case 2.1.

FIG. 14 shows an exemplary embodiment of the second shroud lock mechanism 15 for an autoinjector 1 according to the present invention after final assembly of the drive subassembly 1.2 to the control subassembly 1.1. The needle shroud 7 has been moved further in the proximal direction P relative the front case 2.1 by an assembly jig (not illustrated). In this state, the drive subassembly 1.2 may be assembled to the control subassembly 1.1. Subsequently, the assembly jig is removed and the needle shroud 7 translates in the distal direction D relative to the front case 2.1 under the force of the shroud spring 8 until the shroud rib 7.7 abuts the first plunger boss 10.1. The shroud beam 7.1 is prevented from deflecting radially outward by the stop 2.12 in the front case 2.1.

Figure 15A:
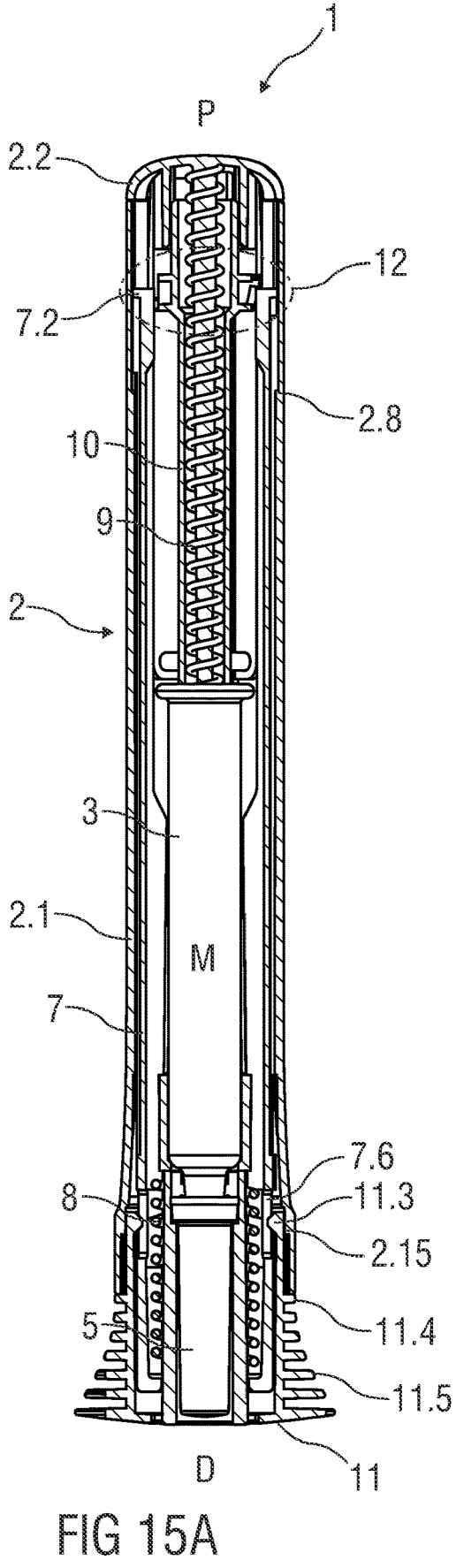
FIG. 15A is a longitudinal section of an exemplary embodiment of an autoinjector according to the present invention after assembly.
Figure 15B:
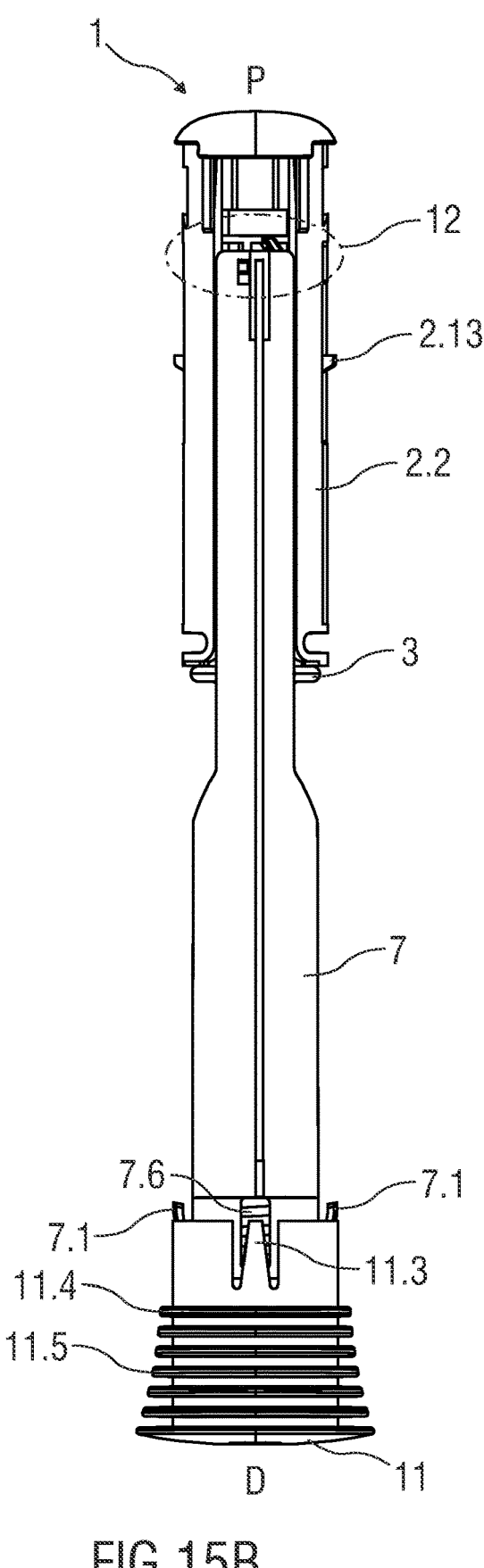
FIG. 15B is a schematic side view of an exemplary embodiment of an autoinjector according to the present invention after assembly.

FIG. 15A is a longitudinal section of an exemplary embodiment of an autoinjector 1 according to the present invention after final assembly, and FIG. 15B is a schematic side view of an exemplary embodiment of an autoinjector 1 according to the present invention after final assembly, wherein the case 2 is removed for clarity.

In an exemplary embodiment, after the final assembly of the drive subassembly 1.2 to the control subassembly 1.1, the autoinjector 1 may be kept in temperature controlled environment (e.g., cold chain storage) to, for example, reduce creep in highly stressed components, e.g. under load from the drive spring 9.

An exemplary sequence of operation of an exemplary embodiment of the autoinjector 1 is as follows:

If applicable, the autoinjector 1 is removed from the packaging. The medicament in the syringe 3 may be visually inspected through a viewing window (not shown), which can be a transparent part of the case 2 or a cut-out in the case 2 aligned with the syringe 3.

Figure 16:
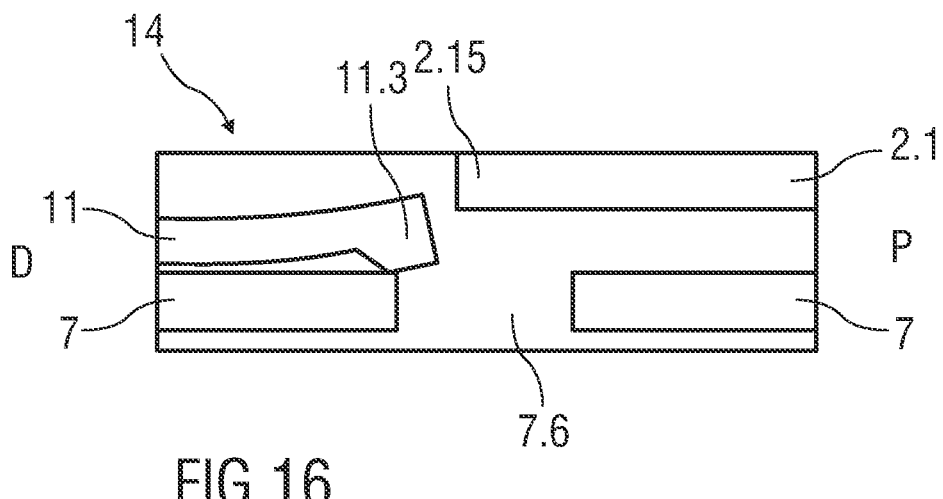
FIG. 16 is a schematic view of an exemplary embodiment of a shroud lock mechanism an exemplary embodiment of an autoinjector according to the present invention prior to use.

The cap 11 is removed by pulling it in the distal direction D away from the case 2. As the cap 11 translates distally relative to the case 2, the bosses 11.2 on the cap 11 frictionally engage the protective needle sheath 5 and pull it off the needle 4 as the cap 11 is pulled in the distal direction D, and the compliant beam 11.3 disengages the aperture 7.6 in the needle shroud 7, as shown in FIG. 16. The compliant beam 11.3 translates distally within the aperture 7.6 until it is no longer abutted radially by the radial stop 2.15 and engages a proximal surface of the aperture 7.6 (which may be ramped) and deflects radially to disengage the aperture 7.6. The syringe 3 is fixed in position relative to the case 2, so pulling the cap 11 in the distal direction D does not cause any axial movement of the syringe 3. In an exemplary embodiment, the syringe 3 is also fixedly rotationally relative to the case 2 (e.g., by an interference fit with the case 2 and/or the needle shroud 7).

Figure 17A:
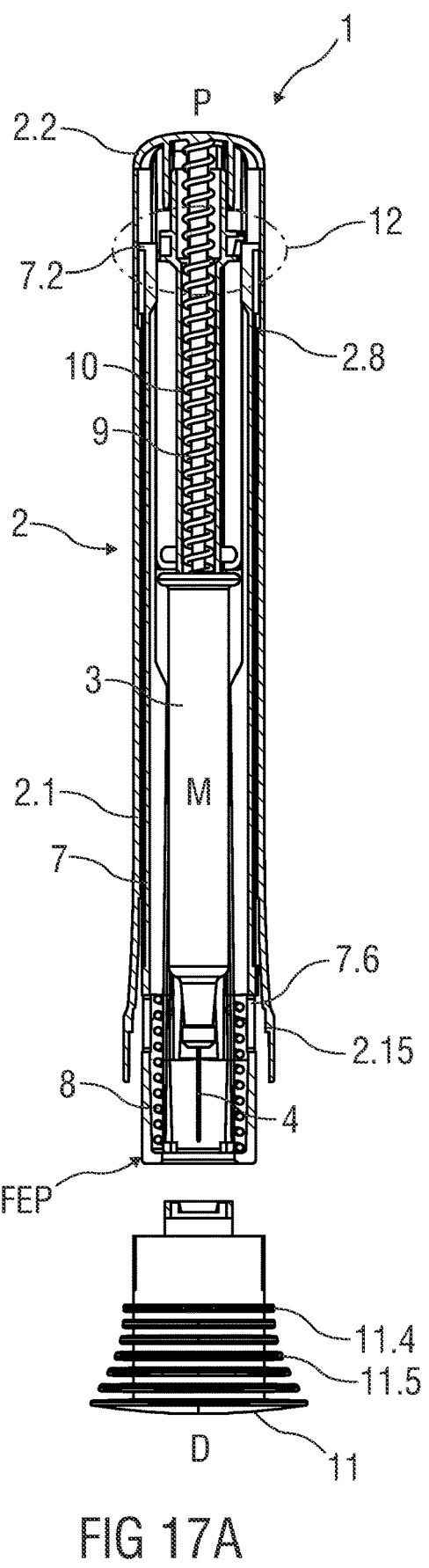
FIG. 17A is a longitudinal section of an exemplary embodiment of a shroud lock mechanism an exemplary embodiment of an autoinjector according to the present invention prior to use.
Figure 17B:
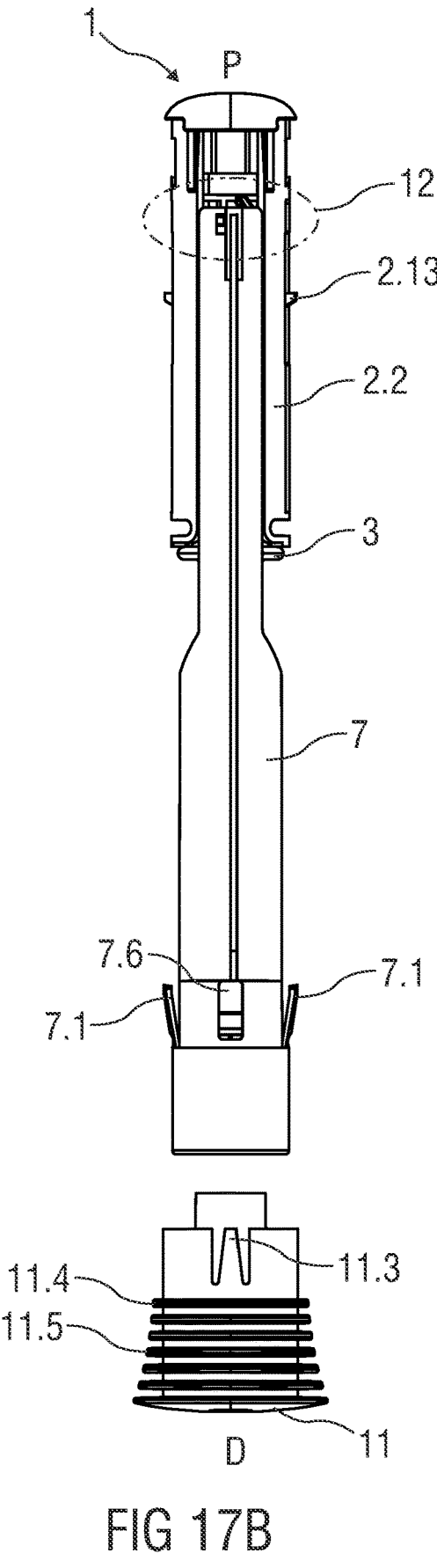
FIG. 17B is a schematic side view of an exemplary embodiment of a shroud lock mechanism an exemplary embodiment of an autoinjector according to the present invention prior to use.

FIG. 17A is a longitudinal section of an exemplary embodiment of the autoinjector 1 according to the present invention prior to use. FIG. 17B is a schematic side view of an exemplary embodiment of the autoinjector 1 according to the present invention prior to use, wherein the case 2 is removed for clarity.

When the cap 11 is removed, the needle shroud 7 is in a first extended position FEP relative to the case 2, protruding from the case 2 in the distal direction D. The first extended position FEP is defined by the first plunger boss 10.1 abutting the shroud rib 7.7.

Figure 18A:
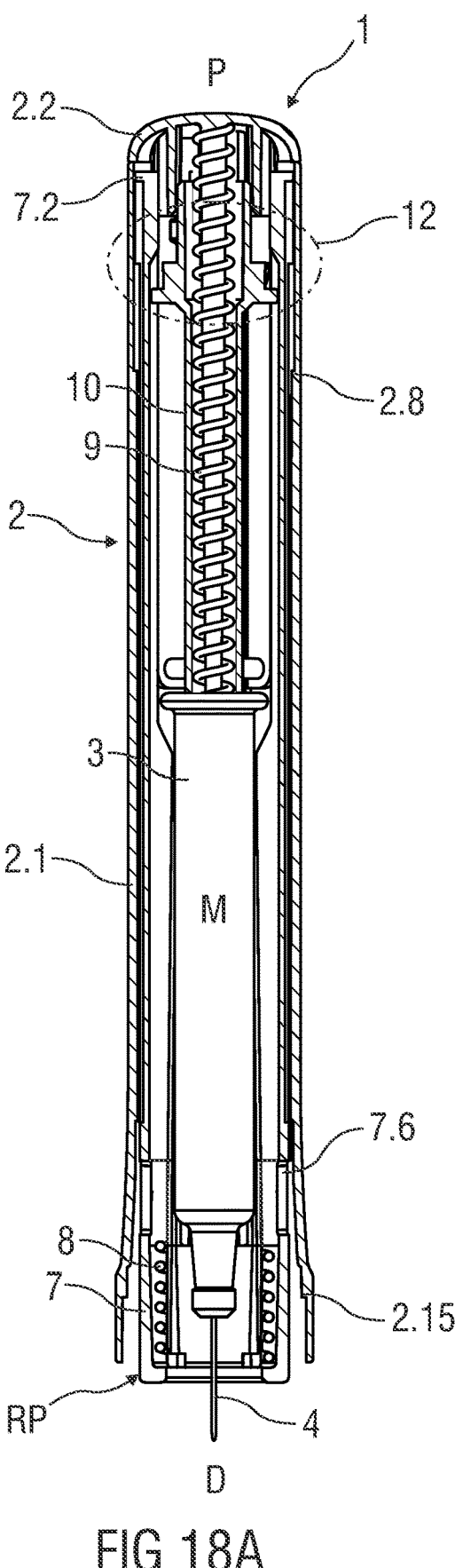
FIG. 18A is a longitudinal section of an exemplary embodiment of an autoinjector according to the present invention during use.
Figure 18B:
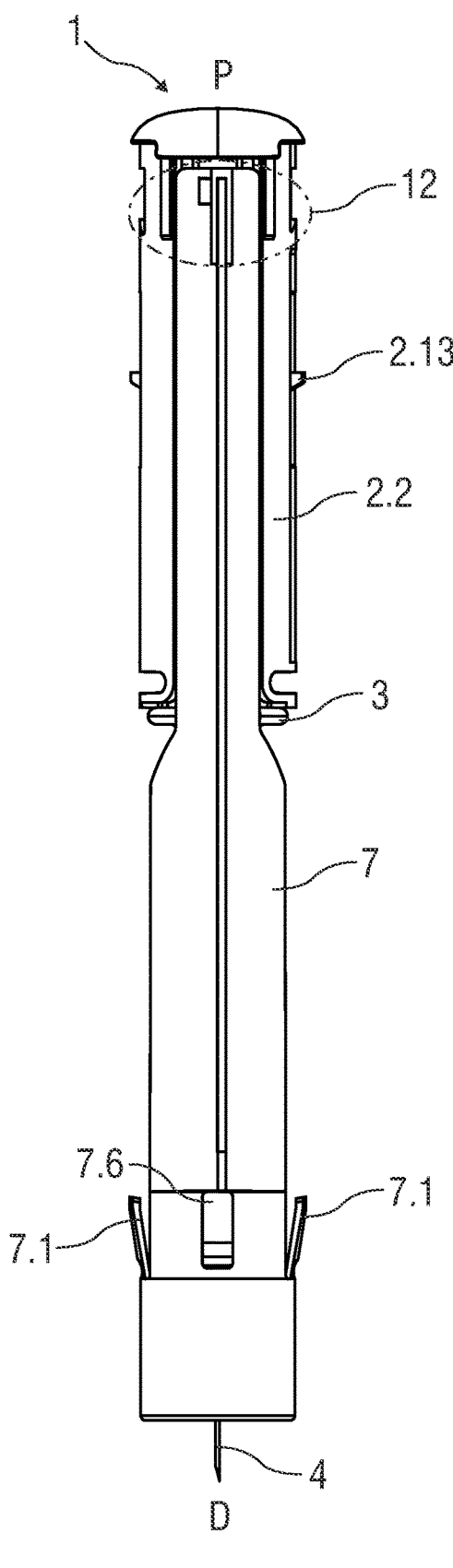
FIG. 18B is a schematic side view of an exemplary embodiment of an autoinjector according to the present invention during use.

FIG. 18A is a longitudinal section of an exemplary embodiment of the autoinjector 1 according to the present invention during use. FIG. 18B is a schematic side view of an exemplary embodiment of the autoinjector 1 according to the present invention during use, wherein the case 2 is removed for clarity.

When the autoinjector 1 is pressed against an injection site, the needle shroud 7 translates proximally relative to the case 2 against the biasing force of the shroud spring 8 from the first extended position FEP to a retracted position RP, as shown in FIGS. 18A and 18B.

Figure 19:
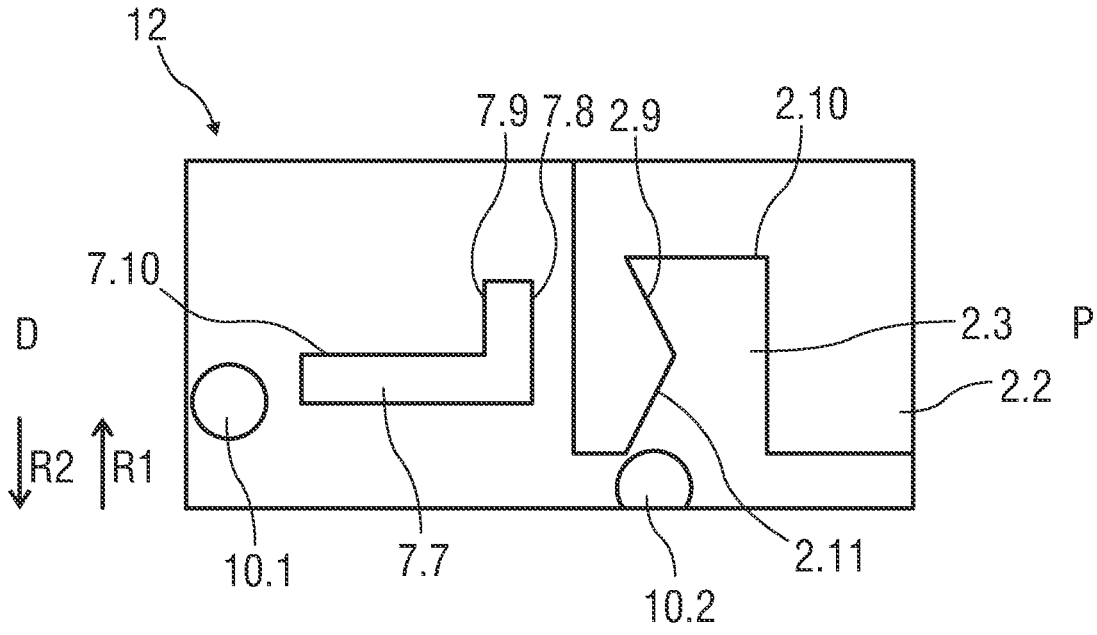
FIG. 19 is a schematic view of an exemplary embodiment of a plunger release mechanism of an exemplary embodiment of an autoinjector according to the present invention during use.

FIG. 19 shows an exemplary embodiment of the plunger release mechanism 12 when the needle shroud 7 is in the retracted position RP. As the needle shroud 7 translates from the first extended position FEP to the retracted position RP, the needle shroud 7 translates distally causing the first plunger boss 10.1 to, starting from the position shown in FIG. 8, ride along the shroud rib 7.7 until it is distal of the shroud rib 7.7. When the first plunger boss 10.1 is distal of the shroud rib 7.7 and may be accommodated by the receiving element, the plunger 10 is no longer prevented from rotating in the second rotational direction R2 relative to the case 2. Thus, the force of the drive spring 9 on the plunger 10 and the engagement of the second plunger boss 10.2 on the second angled surface 2.11 in the case slot 2.3, causes the plunger 10 to rotate relative to the case 2. In an exemplary embodiment, the needle shroud 7 may include an aperture, a recess or a slot proximal of the shroud rib 7.7 to accommodate the first plunger boss 10.1 when the needle shroud 7 is in the retracted position RP and the plunger 10 rotates relative to the case 2.

In an exemplary embodiment, the shroud rib 7.7 (e.g., on the longitudinal face 7.10) may include a resistance feature (e.g., a projection, a ramp, a recess, etc.) adapted to abut the first plunger boss 10.1 as the needle shroud 7 translates from the first extended position FEP to the retracted position RP. When the first plunger boss 10.1 abuts the resistance feature, a tactile feedback is provided in the form of increased resistance to pressing the autoinjector 1 against the injection site. The tactile feedback may be used to indicate that needle 4 will be inserted into the injection site upon further depression of the autoinjector 1 against the injection site. Prior to the needle shroud 7 reaching the retracted position RP, if the autoinjector 1 is removed from the injection site, the needle shroud and reposition as the needle shroud 7 will re-extend to its initial position under the force of the shroud spring 8. When the needle shroud 7 is in the retracted position RP, the needle 4 has been inserted into the injection site. Those of skill in the art will understand that a penetration depth of the needle 4 may be varied by, for example, limiting retraction of the needle shroud 7 relative to the case 2, modifying an axial position of the syringe 3 relative to the case 2, modifying a length of the needle 4, etc. Thus, the autoinjector 1 of the present invention may be used for subcutaneous, intra-dermal and/or intra-muscular injection.

Figure 20A:
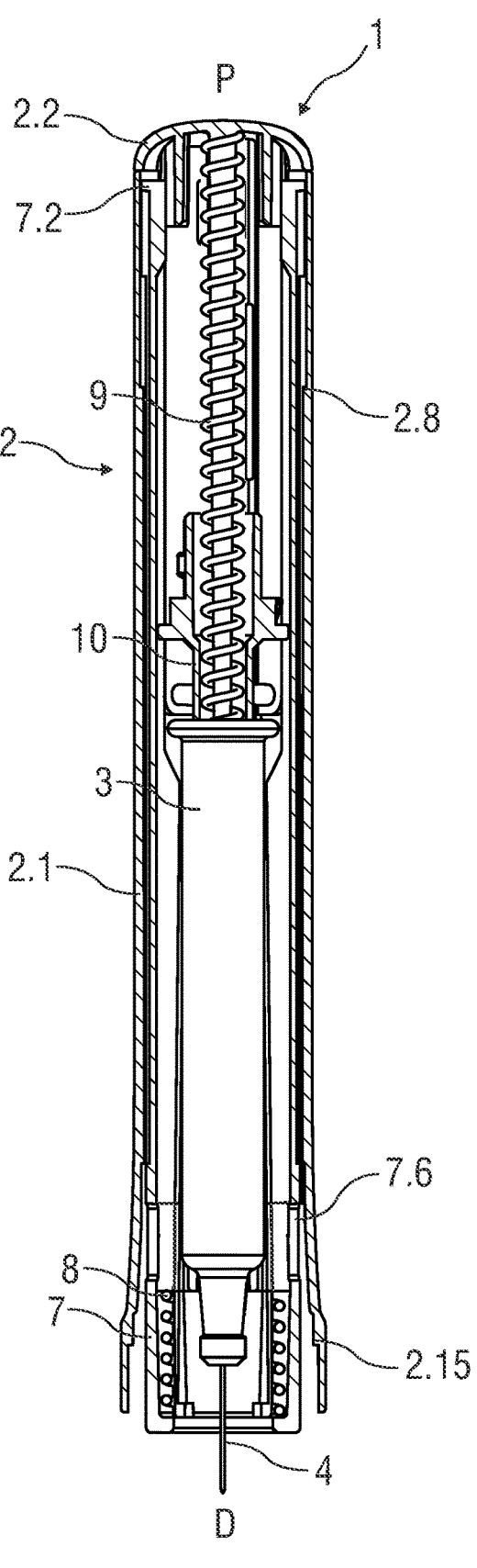
FIG. 20A is a longitudinal section of an exemplary embodiment of an autoinjector according to the present invention during use.
Figure 20B:
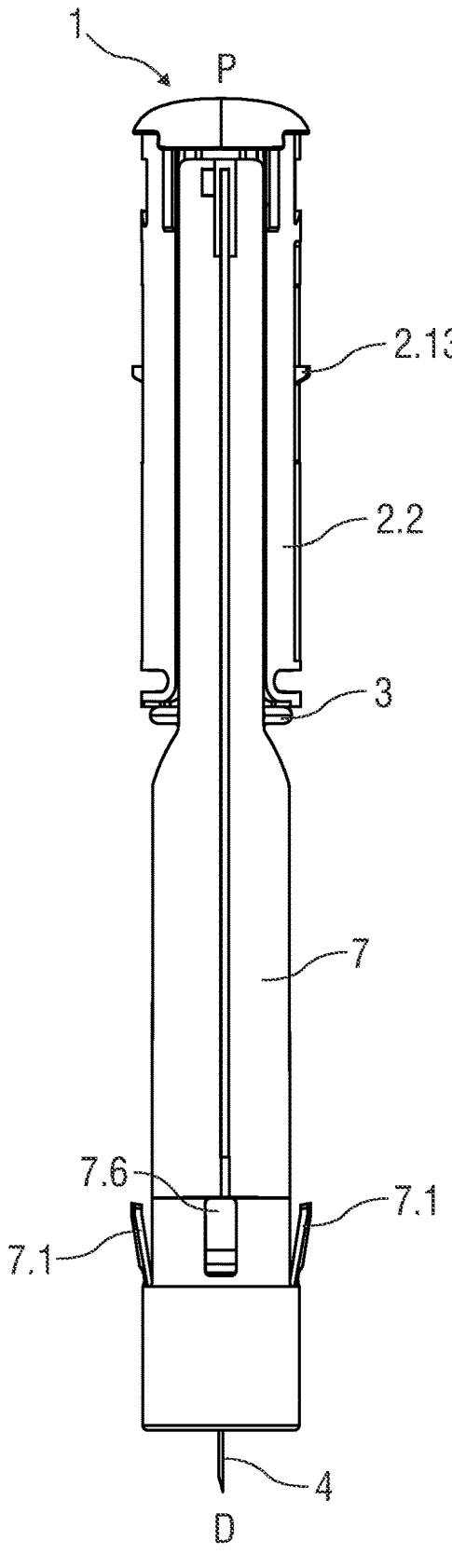
FIG. 20B is a schematic side view of an exemplary embodiment of an autoinjector according to the present invention during use.

FIG. 20A is a longitudinal section of an exemplary embodiment of the autoinjector 1 according to the present invention during use. FIG. 20B is a schematic side view of an exemplary embodiment of the autoinjector 1 according to the present invention during use, wherein the case 2 is removed for clarity.

When the plunger 10 has rotated a sufficient distance in the second rotational direction R2 such that the second plunger boss 10.2 disengages the case slot 2.3, the plunger 10 is free to translate axially, under the force of the drive spring 9, relative to the case 2 to push the stopper 6 to deliver the medicament M from the syringe 3 through the needle 4.

In an exemplary embodiment, disengagement of the first plunger boss 10.1 from the shroud rib 7.7 and/or the second plunger boss 10.2 from the case slot 2.3 may provide an audible feedback indicating that delivery of the medicament M has started. A viewing window in the case 2 may allow for a visual feedback that the plunger 10 is advancing within the syringe 3 for assessing the progress of displacement of the medicament M.

Figure 21A:
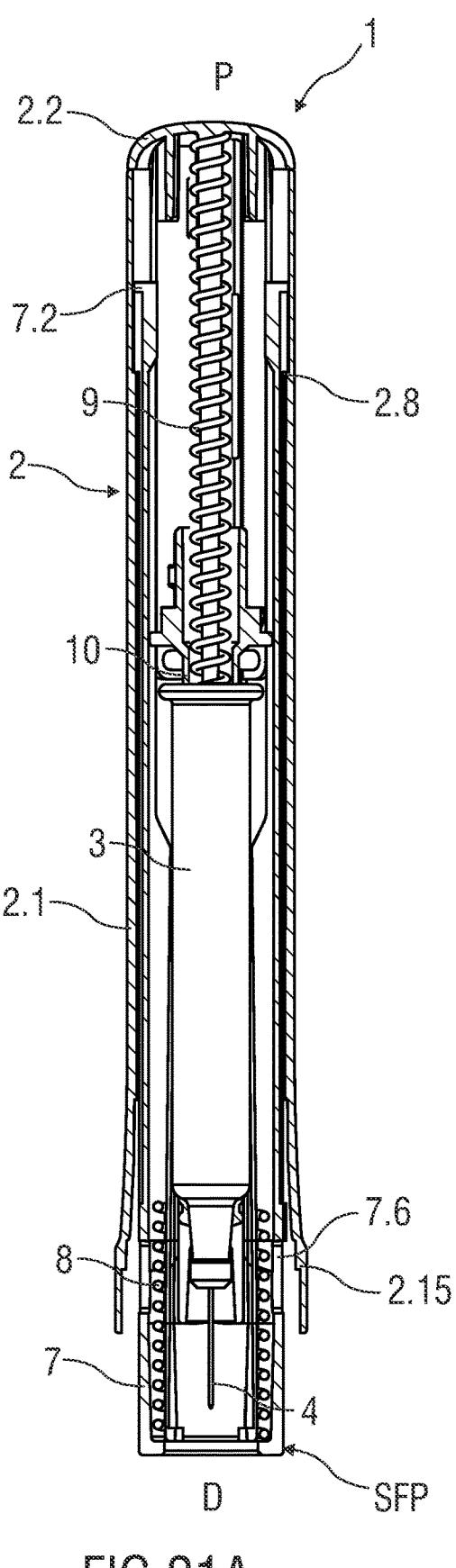
FIG. 21A is a longitudinal section of an exemplary embodiment of an autoinjector according to the present invention after use.
Figure 21B:
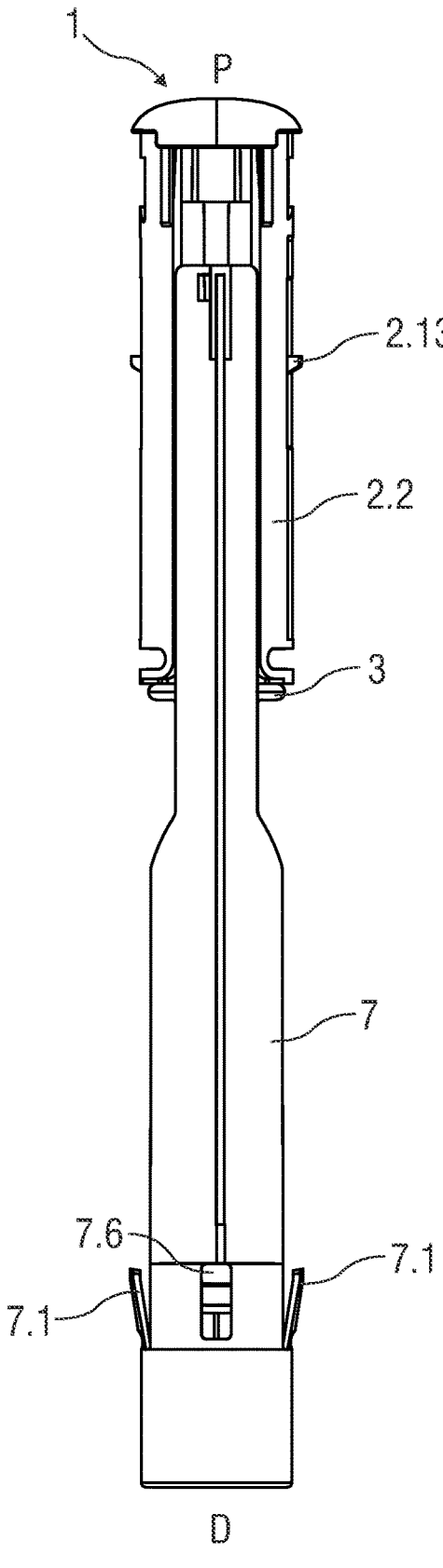
FIG. 21B is a schematic side view of an exemplary embodiment of an autoinjector according to the present invention after use.

FIG. 21A is a longitudinal section of an exemplary embodiment of the autoinjector 1 according to the present invention after use. FIG. 21B is a schematic side view of an exemplary embodiment of the autoinjector 1 according to the present invention after use, wherein the case 2 is removed for clarity.

When the autoinjector 1 is removed from the injection site, the needle shroud 7 translates distally relative to the case 2 from the retracted position RP to a second extended position SEP under the biasing force of the shroud spring 8. In the second extended position SEP, the needle shroud 7 extends beyond a distal tip of the needle 4 and locks in an axial position relative to the case 2. The second extended position SEP prevents needle-stick injury and may also indicate that the autoinjector 1 has been used (because the needle shroud 7 cannot move proximally from the second extended position SEP). In an exemplary embodiment, in the second extended position SEP, the needle shroud 7 protrudes further, e.g. 2 mm, from the case 2 than in the first extended position FEP. The needle shroud 7 may include an indicia (e.g., a red ring, text, a graphic) on a portion which is visually accessible when the needle shroud 7 is in the second extended position SEP but not in the first extended position FEP. The indicia may indicate that the autoinjector 1 has been used.

Figure 22:
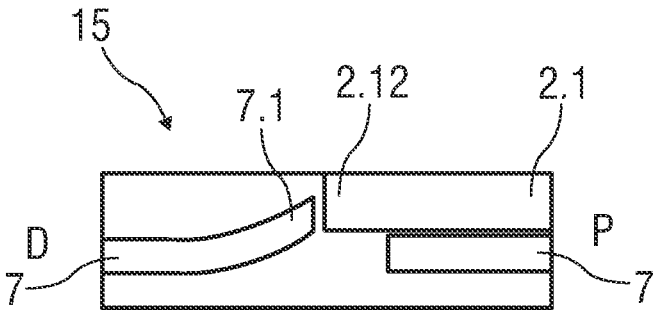
FIG. 22 is a schematic view of an exemplary embodiment of a shroud lock mechanism of an exemplary embodiment of an autoinjector according to the present invention after use.

FIG. 22 is a schematic view of an exemplary embodiment of the second shroud lock mechanism 15 according to the present invention. As the needle shroud 7 translates from the retracted position RP toward the second extended position SEP, the shroud beam 7.1 passes the stop 2.12 in the distal direction D and relaxes radially outwards which is possible as the cap 11 is no longer present. In the second extended position SEP, the needle shroud 7 cannot translate proximally relative to the case 2, because the shroud beam 7.1 abuts the stop 2.12. The needle shroud 7 is thus locked in the second extended position SEP. Extension of the needle shroud 7 distally beyond the second extended position SEP may be prevented by a shroud boss 7.2 on the needle shroud 7 that abuts a case boss 2.8 on the case 2 (see FIG. 1).

FIGS. 23A to 23E are schematic views of another exemplary embodiment of a plunger release mechanism 12 of the autoinjector 1 according to the present invention. The plunger release mechanism 12 is arranged for preventing release of the plunger 10 prior to retraction of the needle shroud 7 relative to the case 2 and for releasing the plunger 10 once the needle shroud 7 is sufficiently retracted. In an exemplary embodiment, the plunger release mechanism 12 comprises the plunger 10, the rear case 2.2, and the needle shroud 7. In this exemplary embodiment, the needle shroud 7 is limited to axial movement relative to the case 2, and the plunger 10 can translate axially and rotate relative to the case 2.

In the exemplary embodiment shown in FIGS. 23A-E, the plunger 10 comprises a first plunger boss 10.1 adapted to engage a shroud rib 7.7 on the needle shroud 7, a second plunger boss 10.2 adapted to engage a case slot 2.3 in the case 2, and a plunger rib 10.3 adapted to engage the shroud rib 7.7 on the needle shroud 7. In an exemplary embodiment, the shroud rib 7.7 is disposed in a plane substantially perpendicular to a longitudinal axis of the case 2. The shroud 7.7 comprises a proximal face 7.8 adapted to engage the plunger rib 10.3, and a distal face 7.9 adapted to engage the first plunger boss 10.1. In an exemplary embodiment, the case slot 2.3 comprises a first angled surface 2.9 adapted to apply a rotational force in a first rotational direction R1 to the second plunger boss 10.2, a wall 2.10 adapted to abut the second plunger boss 10.2 to limit rotation of the plunger 10 relative to the case 2 in the first rotational direction R1, and a transversal surface 2.16 disposed in a plane substantially perpendicular to a longitudinal axis of the case 2.

Figure 23A:
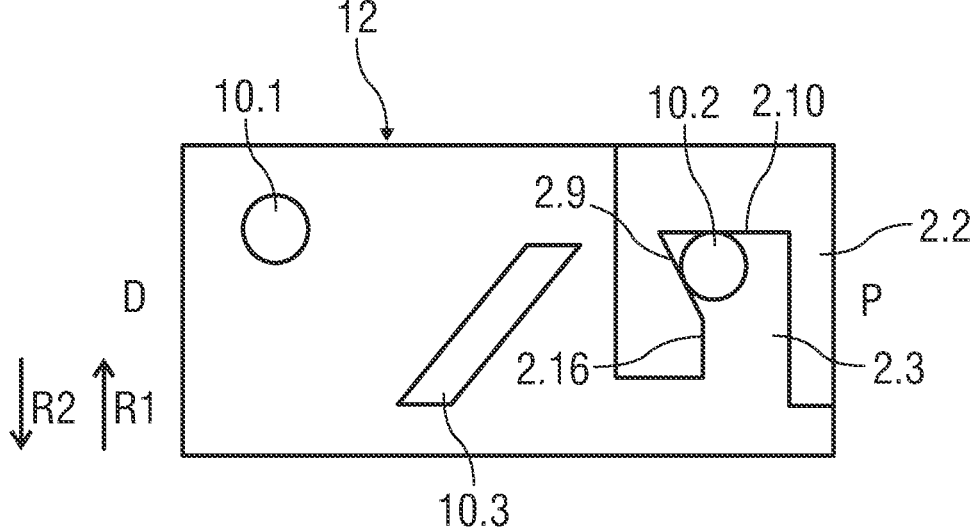
FIGS. 23A-E is a schematic view of another exemplary embodiment of a plunger release mechanism during assembly and before, during and after use.

FIG. 23A is a schematic view of an exemplary embodiment of the plunger release mechanism 12 of the autoinjector 1 according to the present invention during assembly of the drive subassembly 1.2. During assembly of the drive subassembly 1.2, the plunger 10 with the drive spring 9 is inserted into the rear case 2.2. When the second plunger boss 10.2 is axially aligned with the case slot 2.3, the plunger 10 is rotated in the first rotational direction R1 until the second plunger boss 10.2 is moved into the case slot 2.3 until it abuts the wall 2.10. In this position, the first angled surface 2.9 prevents the second plunger boss 10.2 from moving in the second rotational direction R2, and thus prevents the plunger 10 from rotating relative to the case 2.

Figure 23B:
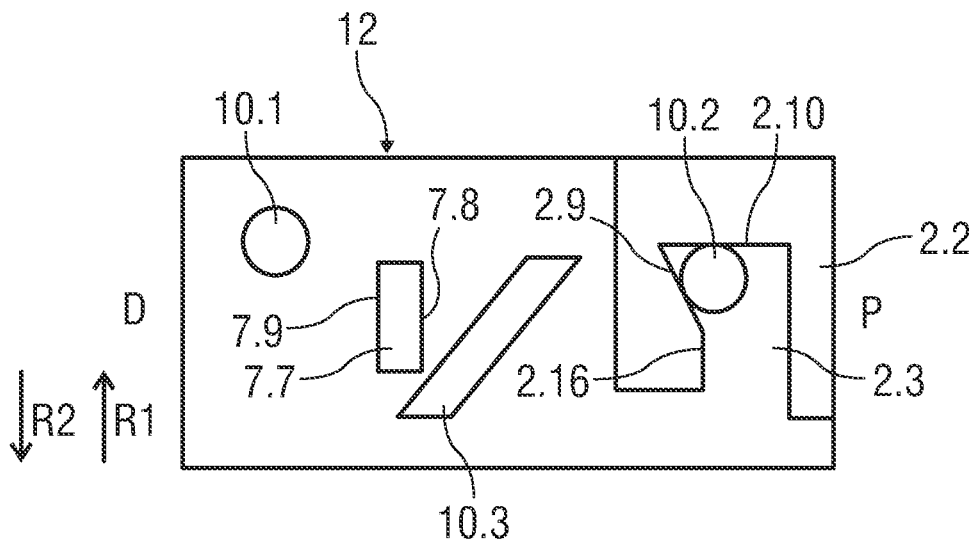
Figure 23C:
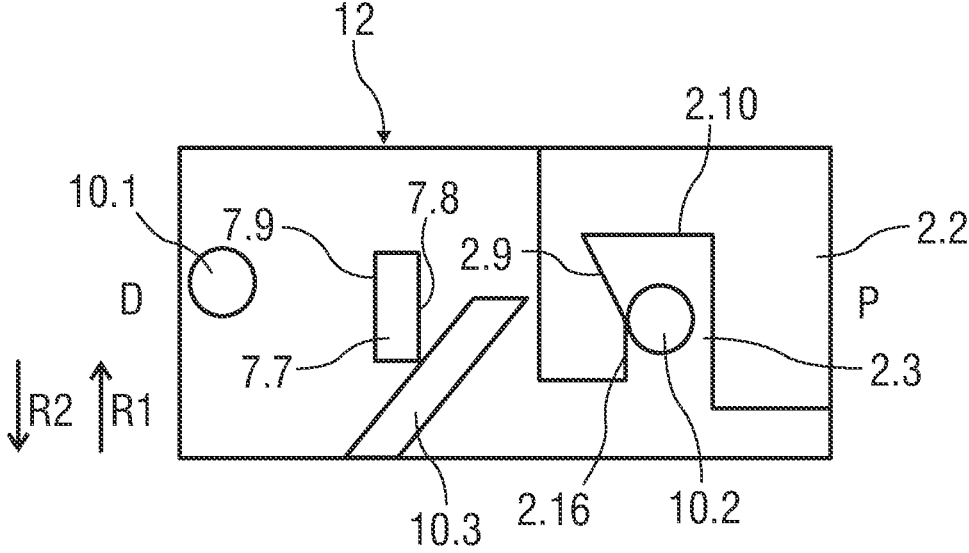

After a syringe 3 (with the protective needle sheath 5 disposed on the needle 4) is inserted into the control assembly 1.1, the drive subassembly 1.2 is coupled to the control subassembly 1.1. In an exemplary embodiment, a pair of resilient beams 2.13 (shown in FIG. 1B) on the rear case 2.2 is adapted to snap into recesses 2.14 (shown in FIG. 3) in the front case 2.1 to lock the drive subassembly 1.2 to the control subassembly 1.1. FIG. 23B shows the drive assembly 1.2 being coupled to the control subassembly 1.1, wherein the needle shroud 7 translates proximally (e.g., by use of an assembly jig) causing the shroud rib 7.7 to abut the plunger rib 10.3. As shown in FIG. 23C, as the needle shroud rib 7.7 pushes the plunger rib 10.3, the angle of the plunger rib 10.3 causes the plunger 10 to rotate relative to the case 2 in the second rotational direction R2, and the second plunger boss 10.2 rides along the first angled surface 2.9 onto the transversal surface 2.16.

Figure 23D:
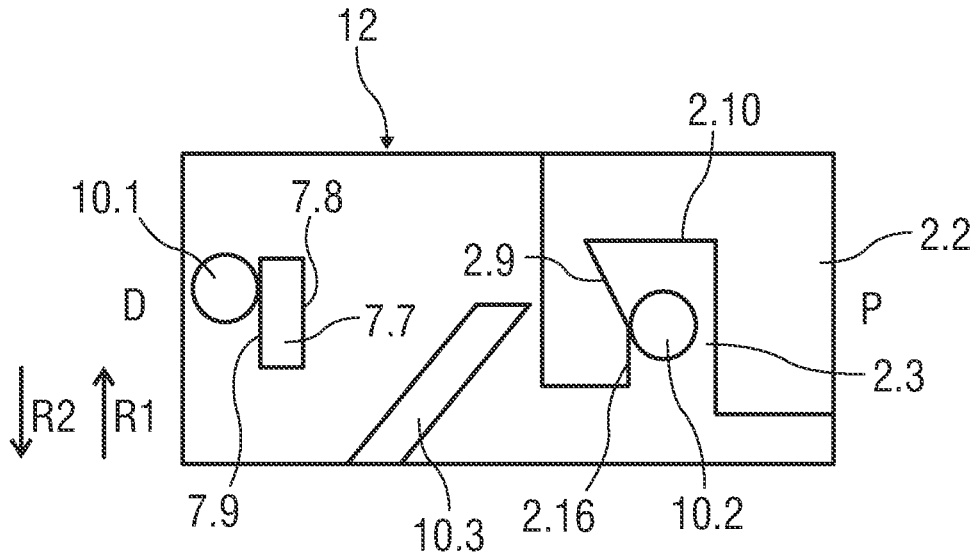

As shown in FIG. 23D, when the needle shroud 7 is released (e.g., by removing the assembly jig), the needle shroud 7 translates in the distal direction D relative to the case 2 under the force of the shroud spring 8 until the shroud rib 7.7 abuts the first plunger boss 10.1. For example, the distal face 7.9 of the shroud rib 7.7 may abut the first plunger boss 10.1 and maintain the needle shroud 7 in an axial position relative to the case 2. The second plunger boss 10.2 is prevented from disengaging the case slot 2.3 as it abuts the transversal surface 2.16 in the distal direction D.

Figure 23E:
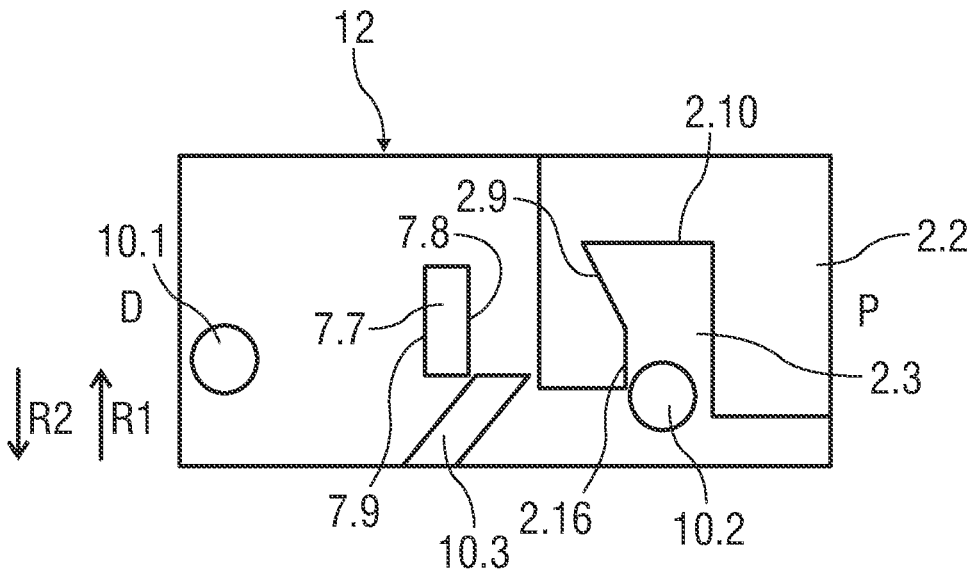

FIG. 23E shows an exemplary embodiment of the plunger release mechanism 12 when the needle shroud 7 is in the retracted position RP. As the needle shroud 7 translates from the first extended position FEP to the retracted position RP, the needle shroud 7 translates distally causing the shroud rib 7.7 to, starting from the position shown in FIG. 23D, ride along the plunger rib 10.3 thereby rotating the second plunger boss 10.2 in the second rotational direction R2 along the transversal surface 2.16 until the second plunger boss 10.2 disengages the case slot 2.3 thus releasing the plunger 10. Then, under the force of the drive spring 9, the plunger 10 translates axially relative to the case 2 to deliver the medicament M from the syringe 3. In this exemplary embodiment, a tactile feedback may be provided in the form of an increase in resistance when the needle shroud 7 abuts and pushes against the plunger rib 10.3. The tactile feedback may indicate that needle insertion will commence or medicament delivery will be initiated if the autoinjector 1 is pressed further against the injection site.

In an exemplary embodiment the transversal surface 2.16 could be replaced by or comprise a concave shape for preventing inadvertent release of the plunger 10.

In another exemplary embodiment, the plunger 10 may not have the first plunger boss 10.1, the plunger rib 10.3 may be disposed at different angle than as described above, and the case slot 2.3 may not be angled relative to a transverse axis of the case 2. In this exemplary embodiment, when the autoinjector 1 is assembled, the plunger 10 is maintained in axial position relative to the case 2, because the second plunger boss 10.2 engages the case slot 2.3. However, the case slot 2.3 may not impart any rotational force on the second plunger boss 10.2 (or, in another exemplary embodiment, the case slot 2.3 may be angled to impart a rotational force on the second plunger boss 10.2 in the first rotational direction R1 to ensure that the second plunger boss 10.2 does not disengage the case slot 2.3 inadvertently).

In an exemplary embodiment, a tamper strip (not shown) may be arranged between the cap 11 and the front case 2.1 when the control subassembly 1.1 is assembled. The tamper strip may be useful for quality assurance.

In an exemplary embodiment, a force required to press the needle shroud 7 may be approximately 2-12 N.

In an exemplary embodiment, the syringe 3 used in the autoinjector 1 may be a syringe capable of containing approximately 1 mL of the medicament M. In another exemplary embodiment, the syringe 3 used in the autoinjector 1 may be a syringe capable of containing approximately 2 mL of the medicament M.

The autoinjector 1 according to the present invention may have an increased shelf-life compared to conventional autoinjectors, because, for example, only the plunger 10 is subjected to the relatively high force of the drive spring 9.

The autoinjector 1 according to the present invention may be used as a platform as the drive spring 9 can be changed to alter a force applied to the plunger 10, e.g., for delivering medicaments with different viscosities drugs or reconstituted medicaments, or changing a time required to inject a dose of the medicament.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4 (1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4 (1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A single use autoinjector, comprising:
a case adapted to receive a medicament container which is operatively coupled or coupleable to a needle, the needle configured to protrude distally from the case before and after a single dispensing operation, wherein the medicament container contains a single dose of a medicament, the case being adapted to hold the medicament container in a fixed position relative to the case when the medicament container is received in the case;
a drive mechanism comprising a plunger and a drive spring configured to supply energy to dispense the single dose of the medicament from the medicament container through the needle in the single dispensing operation; and
a needle shroud movably coupled to the case, the needle shroud configured to protrude distally over a distal end of the needle (i) in a non-locked state of the autoinjector before the single dispensing operation is commenced and (ii) in a locked state after the single dispensing operation,
wherein, in the non-locked state, the needle shroud is movable in the proximal direction relative to the needle and the case, and in the locked state, the needle shroud is prevented from moving in the proximal direction relative to the case by an engagement between a radially resiliently deflectable portion of the needle shroud and a distally facing surface on the case, wherein the radially resiliently deflectable portion extends in a proximal direction from a cylindrical portion of the needle shroud, and an end of the radially resiliently deflectable portion in the locked state is radially outwardly positioned with respect to the end of the radially resiliently deflectable portion in the non-locked state.

2. The single use autoinjector of claim 1, wherein the cylindrical portion is disposed at a distal end of the needle shroud.

3. The single use autoinjector of claim 1, wherein the needle shroud comprises at least one needle shroud leg extending further in the proximal direction than the radially resiliently deflectable portion.

4. The single use autoinjector of claim 3, wherein, in an angular direction, the radially resiliently deflectable portion is disposed between two needle shroud legs of the needle shroud.

5. The single use autoinjector of claim 3, wherein the at least one needle shroud leg has a plunger interaction portion arranged to abut a shroud interaction portion of the plunger of the drive mechanism.

6. The single use autoinjector of claim 5, wherein the plunger interaction portion is arranged in a proximal end section of the at least one needle shroud leg.

7. The single use autoinjector of claim 5, wherein:
the plunger is biased by the drive spring in a rotational direction and in a distal direction in the non-locked state of the needle shroud and, for releasing the plunger for the dispensing operation, the needle shroud is movable in a proximal direction relative to the case from a first position into a release position,
the plunger interaction portion comprises a shroud protrusion abutting a plunger protrusion of the shroud interaction portion of the plunger to prevent rotation of the plunger in the rotational direction in the first position of the needle shroud, and
in the release position, the plunger protrusion no longer abuts the shroud protrusion to release the plunger for the dispensing operation.

8. The single use autoinjector of claim 7, wherein, in the locked state, the needle shroud is in a locked position relative to the case, and wherein the needle shroud protrudes further from the case in the locked position than in the first position.

9. The single use autoinjector of claim 8, wherein the needle shroud protrudes from the case in the release position.

10. The single use autoinjector of claim 8, wherein the autoinjector comprises a cap, the cap being removably coupled to the autoinjector, wherein, when the cap is coupled to the autoinjector, the cap locks the needle shroud such that movement of the needle shroud relative to the case is prevented before the dispensing operation unless the cap is removed, wherein the cap locks the needle shroud by one of or both of:
a) the cap abutting a distal end of the case, and
b) a radially displaceable cap feature engaging the needle shroud.

11. The single use autoinjector of claim 10, wherein, when the cap is being removed, the radially displaceable cap feature is radially outwardly displaced to disengage the needle shroud.

12. The single use autoinjector of claim 1, wherein, in the locked state, the needle shroud is in a locked position relative to the case and, in the locked position, the needle shroud protrudes further from the case than in a non-locked position which the needle shroud has relative to the case in the non-locked state, so as to expose a portion of the needle shroud in the locked position which was covered by the case in the non-locked position.

13. The autoinjector of claim 12, wherein the portion of the needle shroud exposed in the locked position comprises a visually perceivable marking.

14. The single use autoinjector of claim 13, wherein the marking is a graphical marking and indicates that the autoinjector has been used.

15. The single use autoinjector of claim 1, wherein the single use autoinjector comprises the medicament container, the medicament container being a syringe with a needle, and the syringe containing the single dose of the medicament.

16. The single use autoinjector of claim 1, wherein the drive mechanism is configured to supply the energy to dispense the single dose of the medicament from the medicament container through the needle in the single dispensing operation while a portion of the drive spring is inside the plunger.

17. A method for delivering a single dose of a medicament from a single use autoinjector into a subject, the method comprising:

moving a needle shroud of the auto-injector in a proximal direction relative to a case of the auto-injector when the auto-injector is in a non-locked state while the case holds a syringe in a fixed position relative to the case;

after moving the needle shroud in the proximal direction relative to the case and while the case holds the syringe in the fixed position relative to the case, delivering the single dose of the medicament from the syringe into the subject by a plunger of a drive mechanism of the auto-injector being driven by a drive spring of the drive mechanism such that the single dose of the medicament is delivered through a needle of the syringe, the needle configured to protrude distally from the case before and after delivering the medicament; and after delivering the medicament, engaging a radially resiliently deflectable portion of the needle shroud to a surface on the case to change the auto-injector to a locked state in which proximal movement of the needle shroud relative to the case is prevented, wherein the radially resiliently deflectable portion extends in a proximal direction from a cylindrical portion of the needle shroud, and an end of the radially resiliently deflectable portion in the locked state is radially outwardly positioned with respect to the end of the radially resiliently deflectable portion in the non-locked state.

18. The method of claim 17, wherein the drive spring is configured to store energy to drive the single dispensing operation to dispense the single dose of the medicament from the medicament container through the needle in the single dispensing operation.

19. The method of claim 17, wherein the single dose of the medicament is delivered through the needle of the syringe while a portion of the drive spring is inside the plunger.

20. A single use autoinjector, comprising:

a case adapted to receive a medicament container which is operatively coupled or coupleable to a needle, the needle configured to protrude distally from the case before and after a single dispensing operation, wherein the medicament container contains a single dose of a medicament, the case being adapted to hold the medicament container in a fixed position relative to the case when the medicament container is received in the case;

a drive mechanism comprising a drive energy member and a plunger, wherein the drive energy member is configured to supply energy to the plunger to dispense the single dose of the medicament from the medicament container through the needle in the single dispensing operation while a portion of the drive energy member is inside the plunger; and a needle shroud movably coupled to the case, the needle shroud configured to protrude distally over a distal end of the needle (i) in a non-locked state of the autoinjector before the single dispensing operation is commenced and (ii) in a locked state after the single dispensing operation, wherein, in the non-locked state, the needle shroud is movable in the proximal direction relative to the needle and the case, and in the locked state, the needle shroud is prevented from moving in the proximal direction relative to the case by an engagement between the needle shroud and the case, wherein a radially resiliently deflectable portion extends in a proximal direction from a cylindrical portion of the needle shroud, and an end of the radially resiliently deflectable portion in the locked state is radially outwardly positioned with respect to the end of the radially resiliently deflectable portion in the non-locked state.

21. The single use autoinjector of claim 20, wherein the drive energy member is a drive spring in which energy is stored to drive the single dispensing operation to dispense the single dose of the medicament from the medicament container through the needle in the single dispensing operation.

22. The single use autoinjector of claim 20, wherein the engagement is between the resiliently deflectable portion of the needle shroud and a surface on the case.

* * * * *